United States Patent
Kaku

(10) Patent No.: US 10,201,300 B2
(45) Date of Patent: Feb. 12, 2019

(54) PROCESSOR DEVICE, ENDOSCOPE SYSTEM, OPERATION METHOD FOR ENDOSCOPE SYSTEM

(71) Applicant: FUJIFILM Corporation, Tokyo (JP)

(72) Inventor: Toshihiko Kaku, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 503 days.

(21) Appl. No.: 14/587,309

(22) Filed: Dec. 31, 2014

(65) Prior Publication Data

US 2015/0208958 A1 Jul. 30, 2015

(30) Foreign Application Priority Data

Jan. 30, 2014 (JP) .................. 2014-015680

(51) Int. Cl.
*A61B 5/1455* (2006.01)
*A61B 5/1459* (2006.01)
(Continued)

(52) U.S. Cl.
CPC .......... *A61B 5/1459* (2013.01); *A61B 1/0005* (2013.01); *A61B 1/00009* (2013.01);
(Continued)

(58) Field of Classification Search
None
See application file for complete search history.

(56) References Cited

U.S. PATENT DOCUMENTS 5,187,572 A 2/1993 Nakamura et al.
2007/0078299 A1 4/2007 Ayame et al.
(Continued)

FOREIGN PATENT DOCUMENTS

EP 2689712 A1 1/2014
JP 5-84218 A 4/1993
(Continued)

OTHER PUBLICATIONS

Japanese Office Action and English translation thereof dated Dec. 2, 2015 for Application No. 2014-015680.
(Continued)

*Primary Examiner* — Eric Winakur
*Assistant Examiner* — Marjan Fardanesh
(74) *Attorney, Agent, or Firm* — Birch, Stewart, Kolasch & Birch, LLP

(57) ABSTRACT

An endoscope image input unit 60 receives a current endoscope image signal that is output from an endoscope, which is currently inserted into a subject, and is used to calculate the oxygen saturation. A spectral estimation section 70 generates a spectral estimation image by performing spectral estimation processing on a past endoscope image signal that is obtained during the past endoscope insertion and is different from a signal for oxygen saturation calculation. An oxygen saturation calculation section 74 calculates the current oxygen saturation based on the current endoscope image signal, and calculates the past oxygen saturation based on the spectral estimation image. An oxygen saturation image generation section 80 generates a current oxygen saturation image based on the current oxygen saturation, and generates a past oxygen saturation image based on the past oxygen saturation. A monitor 18 displays the current oxygen saturation image and the past oxygen saturation image.

19 Claims, 20 Drawing Sheets

(51) Int. Cl.
  *A61B 1/00* (2006.01)
  *A61B 5/00* (2006.01)
  *G06T 7/00* (2017.01)
  *A61B 1/06* (2006.01)
  *A61B 1/04* (2006.01)

(52) U.S. Cl.
  CPC ............ *A61B 1/043* (2013.01); *A61B 1/0638* (2013.01); *A61B 1/0653* (2013.01); *A61B 5/14551* (2013.01); *A61B 5/7425* (2013.01); *G06T 7/0014* (2013.01)

(56) References Cited

U.S. PATENT DOCUMENTS

| | | |
|---|---|---|
| 2012/0154567 A1 | 6/2012 | Yamaguchi et al. |
| 2012/0157775 A1 | 6/2012 | Yamaguchi |

FOREIGN PATENT DOCUMENTS

| | | |
|---|---|---|
| JP | 6-285050 A | 10/1994 |
| JP | 2007-97709 A | 4/2007 |
| JP | 2007-97710 A | 4/2007 |
| JP | 2009-77765 A | 4/2009 |
| JP | 2012-125501 A | 7/2012 |
| JP | 2012-130429 A | 7/2012 |
| JP | 2012-170774 A | 9/2012 |

OTHER PUBLICATIONS

Extended European Search Report for European Application No. 14200395.3, dated Jun. 17, 2015.
European Office Action, dated Jul. 26, 2018, for corresponding European Application No. 14200395.3.

PROCESSOR DEVICE, ENDOSCOPE SYSTEM, OPERATION METHOD FOR ENDOSCOPE SYSTEM

CROSS-REFERENCE TO RELATED APPLICATIONS

The present application claims priority under 35 U.S.C. § 119 to Japanese Patent Application No. 2014-015680, filed on Jan. 30, 2014, all of which are hereby expressly incorporated by reference into the present application.

BACKGROUND OF THE INVENTION

1. Field of the Invention

The present invention relates to a processor device, an endoscope system, and an operation method for an endoscope system for displaying a past image and a current image simultaneously.

2. Description of the Related Art

In the medical field, it is common to perform diagnosis using an endoscope system including a light source device, an endoscope, and a processor device. In the diagnosis using an endoscope system, in order to observe the progress of the lesion, not only a current image output from an endoscope, which is currently inserted into the subject, but also a past image obtained during the past endoscope insertion is displayed (for example, refer to JP2012-170774A).

SUMMARY OF THE INVENTION

When observing the progress of the lesion, if a current or past image is a normal observation image obtained using white light, it is difficult to understand a change of the lesion from the normal observation image. Therefore, a method can be considered in which the change of the lesion can be easily understood by simultaneously displaying current and past oxygen saturation images using the fact that the lesion, such as cancer, is in a low oxygen state in which the oxygen saturation is low, the current and past oxygen saturation images expressing the oxygen state of the lesion with a pseudo-color. Here, a case is assumed in which a primary examination using an endoscope is performed in a clinic or a community hospital where an endoscope having an oxygen saturation measurement function is not provided and a subsequent second examination is performed in a large-scale hospital where an endoscope having an oxygen saturation measurement function is provided. In this case, since an image (past image) used in the primary examination is assumed to be mostly a normal observation image, it is difficult to display the current and past oxygen saturation images simultaneously when observing the progress of the lesion at the time of secondary examination. For this reason, there is a demand for displaying the current and past oxygen saturation images simultaneously even if the past image is an image other than an oxygen saturation image, such as a normal observation image.

It is an object of the invention to provide a processor device, an endoscope system, and an operation method for an endoscope system for displaying current and past oxygen saturation images simultaneously even if the past image is an image other than an oxygen saturation image, such as a normal observation image.

In order to achieve the aforementioned object, a processor device of the invention generates a spectral estimation image from a normal observation image and calculates a first oxygen saturation from the spectral estimation image. A spectral estimation image is generated from a normal observation image, a first oxygen saturation is calculated from the spectral estimation image, and a first oxygen saturation image is generated from the first oxygen saturation.

An endoscope system of the invention includes the processor device of the invention described above, and the first oxygen saturation image and a second oxygen saturation image based on a second oxygen saturation are displayed. It is preferable that the second oxygen saturation be an oxygen saturation calculated based on a different image from an image used to calculate the first oxygen saturation, for example.

It is preferable to further include a comparison unit that compares the first oxygen saturation with the second oxygen saturation. It is preferable to further include an oxygen saturation correction unit that corrects at least one of the first and second oxygen saturations based on a comparison result of the comparison unit. It is preferable that the oxygen saturation correction unit correct at least one of the first and second oxygen saturations using gain processing and/or shift processing for oxygen saturation correction. It is preferable to further include a determination unit that determines whether or not to correct at least one of the first and second oxygen saturations based on a comparison result of the comparison unit. It is preferable to further include a coefficient correction unit that corrects a matrix coefficient based on a comparison result of the comparison unit, the matrix coefficient being used to generate the spectral estimation image.

It is preferable to further include: a display processing unit that performs display processing for displaying a specific range and a range outside the specific range in different display methods in the first oxygen saturation image and displaying a specific range and a range outside the specific range in different display methods in the second oxygen saturation image, the first oxygen saturation in the specific range of the first oxygen saturation image being set in advance and the second oxygen saturation in the specific range of the second oxygen saturation image being set in advance; and a boundary value correction unit that corrects a boundary value of the specific range based on a comparison result of the comparison unit.

It is preferable to further include a feature point extraction unit that extracts feature points from the normal observation image and extracts feature points from a specific image used to calculate the second oxygen saturation, and the comparison unit is preferably a first comparison unit that compares an oxygen saturation of a first feature point among the feature points of the normal observation image with an oxygen saturation of a second feature point among the feature points of the specific image or among feature points of an oxygen saturation numerical image, the second feature point having the same feature quantity as the first feature point. It is preferable to further include a feature point extraction unit that extracts feature points from the normal observation image and extracts feature points from an oxygen saturation numerical image having numerical information of the second oxygen saturation for each pixel, and the comparison unit is preferably a first comparison unit that compares an oxygen saturation of a first feature point among the feature points of the normal observation image with an oxygen saturation of a second feature point among the feature points of the oxygen saturation numerical image, the second feature point having the same feature quantity as the first feature point.

It is preferable that the first comparison unit perform the comparison based on a difference between the oxygen saturation of the first feature point and the oxygen saturation of the second feature point. It is preferable that the comparison unit be a second comparison unit that compares a distribution of the first oxygen saturation with a distribution of the second oxygen saturation. It is preferable to further include a difference image generation unit that generates a difference image by imaging a difference between the first and second oxygen saturations or a difference between the first and second oxygen saturation images, and the difference image is preferably displayed.

An operation method for an endoscope system of the invention includes: a step of generating a spectral estimation image by performing spectral estimation processing on a normal observation image with a spectral estimation unit; a step of calculating a first oxygen saturation based on the spectral estimation image with an oxygen saturation calculation unit; a step of generating a first oxygen saturation image from the first oxygen saturation, calculating a second oxygen saturation from specific image information that is different from an image used to calculate the first oxygen saturation, and generating a second oxygen saturation image from the second oxygen saturation with an oxygen saturation image generation unit; and a step of displaying the first oxygen saturation image and the second oxygen saturation image with a display unit.

According to the endoscope system, the processor device, and the operation method for an endoscope system of the invention, it is possible to display the current and past oxygen saturation images simultaneously even if the past image is an image other than an oxygen saturation image, such as a normal observation image.

DESCRIPTION OF THE PREFERRED EMBODIMENTS

First Embodiment

Figure 1:
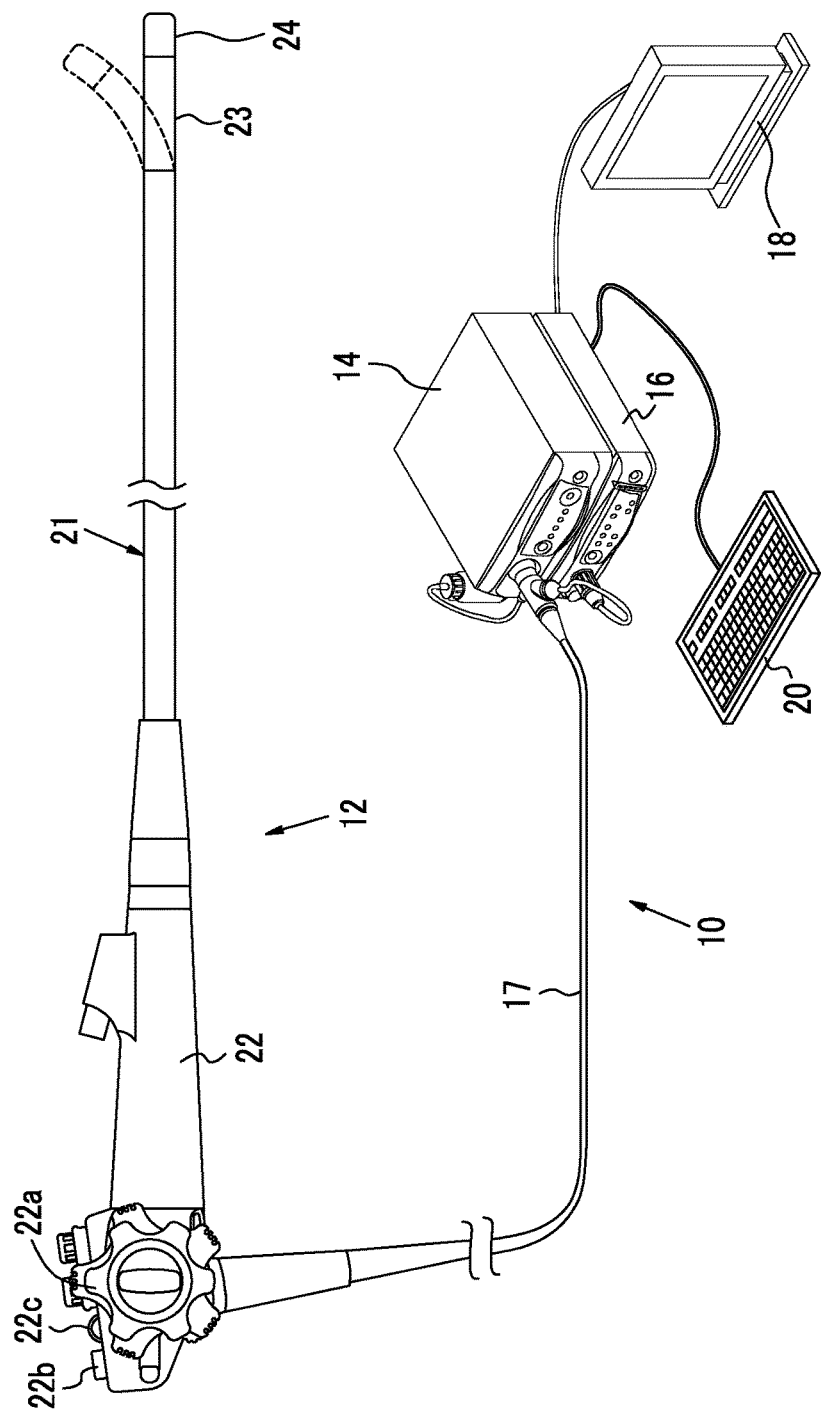
FIG. 1 is an external view of an endoscope system.

As shown in FIG. 1, an endoscope system 10 according to a first embodiment includes an endoscope 12, a light source device 14, a processor device 16, a monitor 18 (display unit), and a console 20. The endoscope 12 is optically connected to the light source device 14 and electrically connected to the processor device 16 through a universal cord 17. The endoscope 12 includes an insertion portion 21 that is inserted into a subject, an operating portion 22 provided at the base end of the insertion portion 21, and a bending portion 23 and a distal portion 24 that are provided at the distal side of the insertion portion 21. By operating an angle knob 22a of the operating portion 22, the bending portion 23 is bent. The distal portion 24 can be directed in a desired direction by the bending operation.

In addition to the angle knob 22a, a mode selector SW 22b, a zoom operation portion 22c, and a freeze button (not shown) for saving a still image are provided in the operating portion 22. The mode selector SW 22b is used for a switching operation between two modes of a normal observation mode and a special observation mode. The normal observation mode is a mode in which a normal observation image obtained by full-color imaging of an observation target in the subject is displayed on the monitor 18. The special observation mode is a mode in which an oxygen saturation image obtained by imaging of the oxygen saturation of blood hemoglobin of the observation target is displayed on the monitor 18.

In the normal observation mode or the special observation mode, either a one-image display mode in which only a current image output from the endoscope 12 that is currently inserted into the subject is displayed on the monitor 18 or a two-image display mode in which a current image and a past image, which was obtained during the past endoscope insertion, are simultaneously displayed can be set by using the console 20. The zoom operation portion 22c is used for a zooming operation for driving a zoom lens 47 (refer to FIG. 2) in the endoscope 12 to magnify the observation target.

The processor device 16 is electrically connected to the monitor 18 and the console 20. The monitor 18 displays an image, such as a normal observation image or an oxygen saturation image, and information regarding the image. The console 20 functions as a user interface (UI) for receiving an input operation, such as a function setting.

Figure 2:
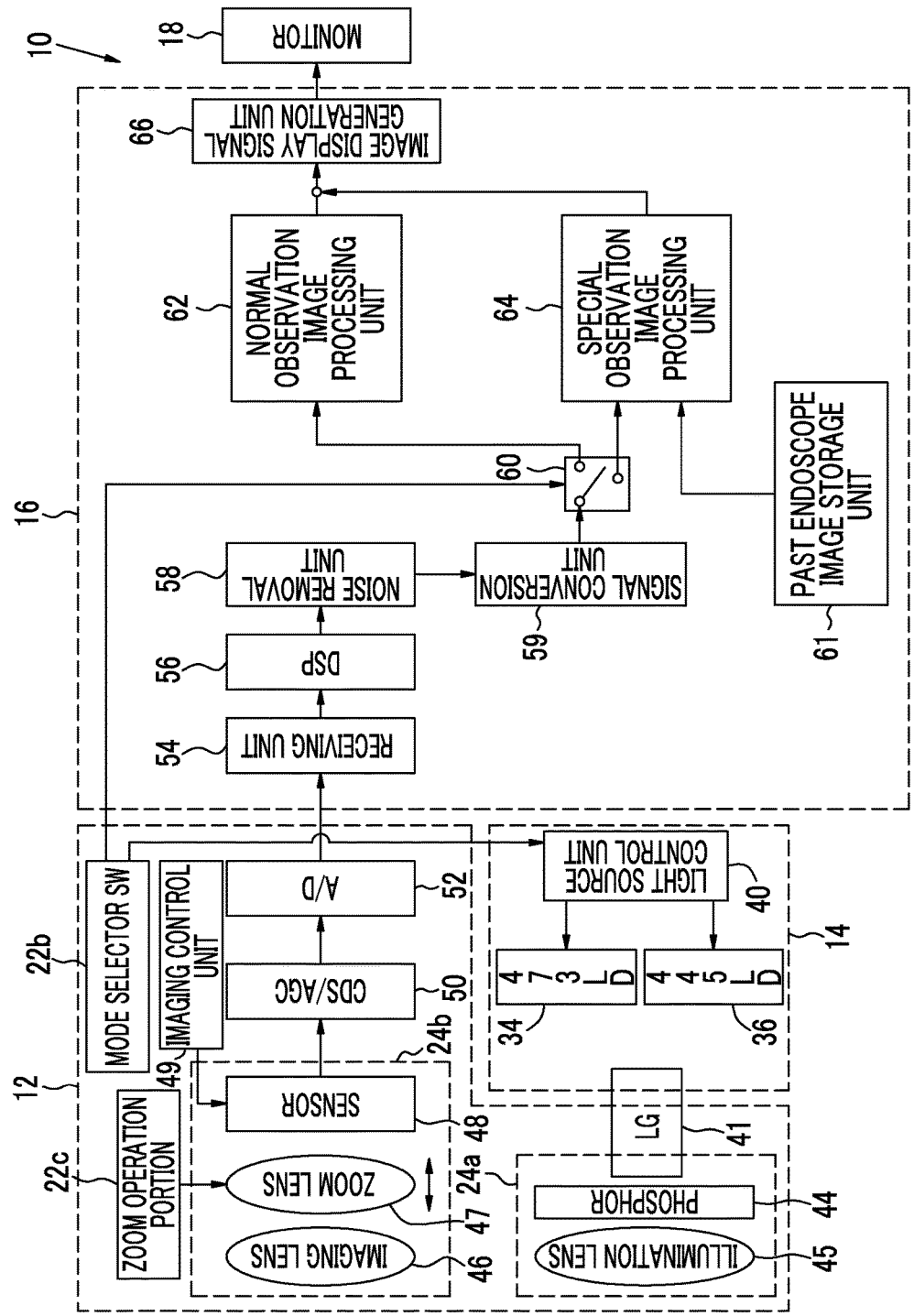
FIG. 2 is a block diagram of an endoscope system according to a first embodiment.

As shown in FIG. 2, the light source device 14 includes, as light emitting sources, a first blue laser light source (473 LD (laser diode)) 34 that emits first blue laser light having a center wavelength of 473 nm and a second blue laser light source (445 LD) 36 that emits second blue laser light having a center wavelength of 445 nm. The emission of the light source devices 34 and 36 is separately controlled by a light source control unit 40. For this reason, the light intensity ratio between light emitted from the first blue laser light source 34 and light emitted from the second blue laser light source 36 can be freely changed.

The light source control unit 40 turns on the second blue laser light source 36 in the normal observation mode. On the other hand, in the special observation mode, the light source control unit 40 turns on the first blue laser light source 34 and the second blue laser light source 36 alternately. In addition, it is preferable that the half-width of each of the first and second blue laser light beams be set to about ±10 nm. As the first blue laser light source 34 and the second blue laser light source 36, a broad area type InGaN-based laser diode can be used, or an InGaNAs-based laser diode or a GaNAs-based laser diode can be used. In addition, as the light sources, it is possible to use a structure using a light emitter, such as a light emitting diode.

The first and second blue laser light beams emitted from the light sources 34 and 36 are incident on a light guide (LG) 41 through optical members, such as a condensing lens, an optical fiber, and a multiplexer (none are shown). The light guide 41 is built into the endoscope 12 and the universal cord 17. The light guide 41 causes the first and second blue laser light beams to propagate from the light sources 34 and 36 to the distal portion 24 of the endoscope 12 therethrough. As the light guide 41, a multi-mode fiber can be used. As an example, it is possible to use a small-diameter fiber cable having a diameter of ϕ0.3 mm to ϕ0.5 mm that includes a core with a diameter of 105 µm, a cladding with a diameter of 125 µm, and a protective layer as an outer skin.

The distal portion 24 of the endoscope 12 includes an illumination optical system 24a and an imaging optical system 24b. A phosphor 44 and an illumination lens 45 are provided in the illumination optical system 24a. The first and second blue laser light beams are incident on the phosphor 44 from the light guide 41. The phosphor 44 emits fluorescence due to the first or second blue laser light emitted thereto. Some of the first or second blue laser light beams are transmitted through the phosphor 44. The light emitted from the phosphor 44 is emitted to the observation target through the illumination lens 45.

Figure 3:
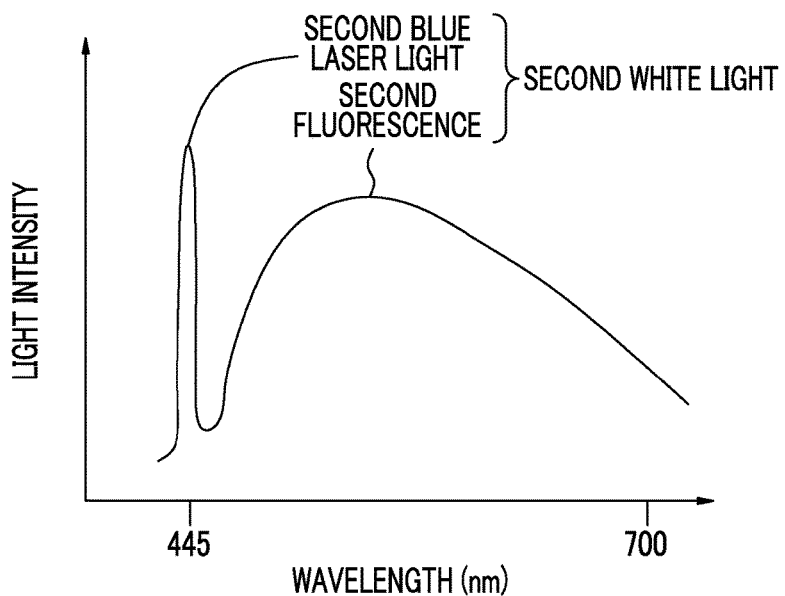
FIG. 3 is a graph showing the spectrum of light emitted in a normal observation mode.

In the normal observation mode, the second blue laser light is incident on the phosphor 44. Accordingly, white light having a spectrum shown in FIG. 3 (second white light) is emitted to the observation target as illumination light. The second white light is configured to include second blue laser light and second fluorescence of green to red that is excited and emitted from the phosphor 44 by the second blue laser light. Accordingly, the wavelength range of the second white light is the entire visible light region.

Figure 4:
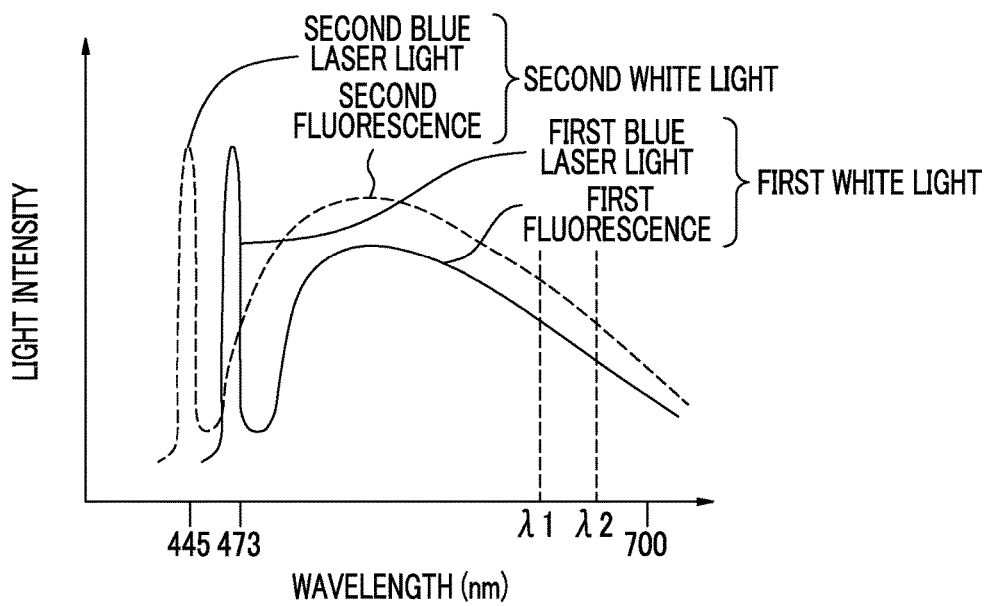
FIG. 4 is a graph showing the spectrum of light emitted in a special observation mode.

On the other hand, in the special observation mode, the first blue laser light and the second blue laser light are alternately incident on the phosphor 44. Therefore, first white light and second white light having the spectrums shown in FIG. 4 are alternately emitted to the observation target. The first white light is configured to include first blue laser light and first fluorescence of green to red that is excited and emitted from the phosphor 44 by the first blue laser light. Accordingly, the wavelength range of the first white light is the entire visible light region. The second white light is the same as the second white light emitted in the normal observation mode.

The first fluorescence and the second fluorescence have almost the same waveform (shape of the spectrum), and the ratio between the intensity ($I1(\lambda)$) of the first fluorescence and the intensity ($I2(\lambda)$) of the second fluorescence (hereinafter, referred to as an inter-frame intensity ratio) is the same at any wavelength $\lambda$. For example, it is $I2(\lambda1)/I1(\lambda1)=I2(\lambda2)/I1(\lambda2)$. Since the inter-frame intensity ratio $I2(\lambda)/I1(\lambda)$ affects the calculation accuracy of the oxygen saturation, the inter-frame intensity ratio $I2(\lambda)/I1(\lambda)$ is accurately controlled by the light source control unit 40 such that the intensity ratio between reference frames set in advance is maintained.

As the phosphor 44, it is preferable to use a phosphor that absorbs some of the first and second blue laser light beams and includes a plurality of kinds of phosphors (for example, a YAG-based phosphor or a phosphor, such as BAM ($BaMgAl_{10}O_{17}$)) that are excited to emit green to red light beams. If a semiconductor light emitting element is used as a light source for exciting the phosphor 44 as in the present embodiment, it is possible to obtain high-intensity first and second white light beams with high luminous efficiency. In addition, it is possible to easily adjust the intensity of the white light and to suppress changes in color temperature and chromaticity.

The imaging optical system 24b of the endoscope 12 includes an imaging lens 46, the zoom lens 47, and a sensor 48 (refer to FIG. 2). Reflected light from the observation target is incident on the sensor 48 through the imaging lens 46 and the zoom lens 47. Then, a reflected image of the observation target is formed on the sensor 48. The zoom lens 47 is moved between the tele end and the wide end by operating the zoom operation portion 22c. When the zoom lens 47 is moved to the tele end side, the reflected image of the observation target is magnified. On the other hand, when the zoom lens 47 is moved to the wide end side, the reflected image of the observation target is reduced. In addition, when magnified observation is not performed (at the time of non-magnified observation), the zoom lens 47 is disposed at the wide end. When performing magnified observation, the zoom lens 47 is moved from the wide end to the tele end side by operating the zoom operation portion 22c.

The sensor 48 is a color imaging device, and captures a reflected image of the observation target and outputs the image signal. The sensor 48 is a charge coupled device (CCD) image sensor. In addition, the sensor 48 includes RGB pixels in which RGB color filters are provided on the imaging surface, and outputs image signals of three colors of R, and B by performing photoelectric conversion with the pixels of respective colors of RGB.

Figure 5:
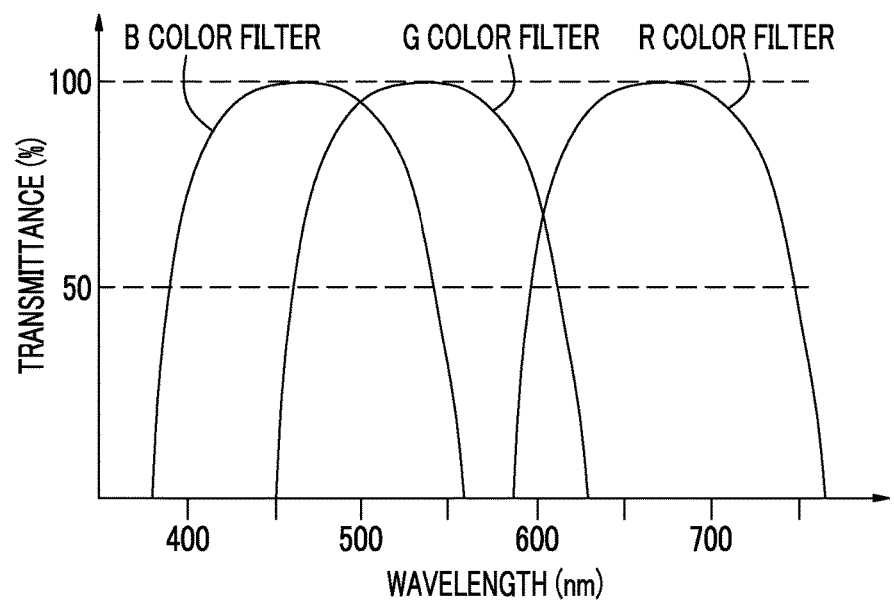
FIG. 5 is a graph showing the spectral transmittance of an RGB color filter.

As shown in FIG. 5, the B color filter has a spectral transmittance of 380 nm to 560 nm, the G color filter has a spectral transmittance of 450 nm to 630 nm, and the R color filter has a spectral transmittance of 580 nm to 760 nm.

Accordingly, when the second white light is emitted to the observation target in the normal observation mode, the second blue laser light and some of green components of the second fluorescence are incident on the B pixel, some of green components of the second fluorescence are incident on the G pixel, and red components of the second fluorescence are incident on the R pixel. However, since the emission intensity of the second blue laser light is significantly larger than that of the second fluorescence, most of the B image signal output from the B pixel is occupied by the reflected light components of the second blue laser light.

On the other hand, when the first white light is emitted to the observation target in the special observation mode, the first blue laser light and some of green components of the first fluorescence are incident on the B pixel, some of green components of the first fluorescence are incident on the G pixel, and red components of the first fluorescence are incident on the R pixel. However, since the emission intensity of the first blue laser light is significantly larger than that of the first fluorescence, most of the B image signal is occupied by the reflected light components of the first blue laser light. Light incidence components in the respective RGB pixels when the second white light is emitted to the observation target in the special observation mode are the same as those in the normal observation mode.

As the sensor 48, it is also possible to use a so-called complementary color image sensor including complementary color filters of C (cyan), M (magenta), Y (yellow), and G (green) on the imaging surface. When using the complementary color image sensor as the sensor 48, a color converter that performs color conversion from image signals of four colors of CMYG to image signals of three colors of RGB is preferably provided in the endoscope 12, the light source device 14, or the processor device 16. In this manner, even when complementary color image sensors are used, it is possible to obtain the image signals of three colors of RGB from the image signals of four colors of CMYG by color conversion.

Figure 6:
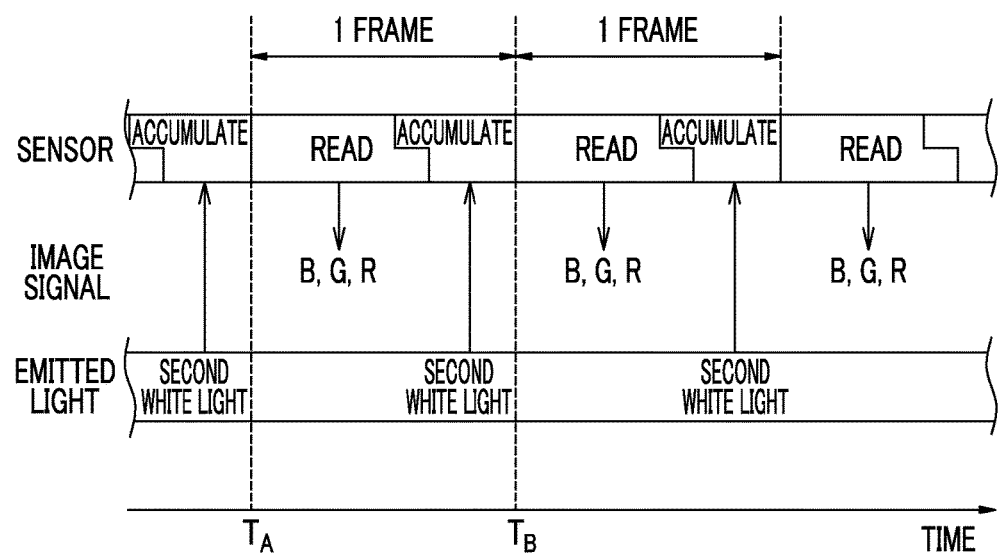
FIG. 6 is an explanatory diagram showing the imaging control in the normal observation mode when a sensor is a CCD.

An imaging control unit 49 performs imaging control of the sensor 48. As shown in FIG. 6, in the normal observation mode, an observation target illuminated by the second white light is imaged by the sensor 48 every period of one frame (hereinafter, simply referred to as one frame). Then, the RGB image signals are output from the sensor 48 for each frame. The RGB image signals are used for the generation of a normal observation image. In the present embodiment, the sensor 48 is a CCD image sensor. Accordingly, one frame is a period of the length from the end (time $T_A$) of a charge accumulation period (also referred to as an exposure period) to the end of the next charge accumulation period (time $T_B$), for example. In addition, since the sensor 48 is a CCD image sensor, one frame is divided into a reading period and a charge accumulation period in FIG. 6. However, the approximately entire one frame can be set as a charge accumulation period, and signal charges accumulated in the previous frame can also be read during the accumulation of signal charges. The imaging control unit 49 also performs control, such as the adjustment of the length of the charge accumulation period.

Figure 7:
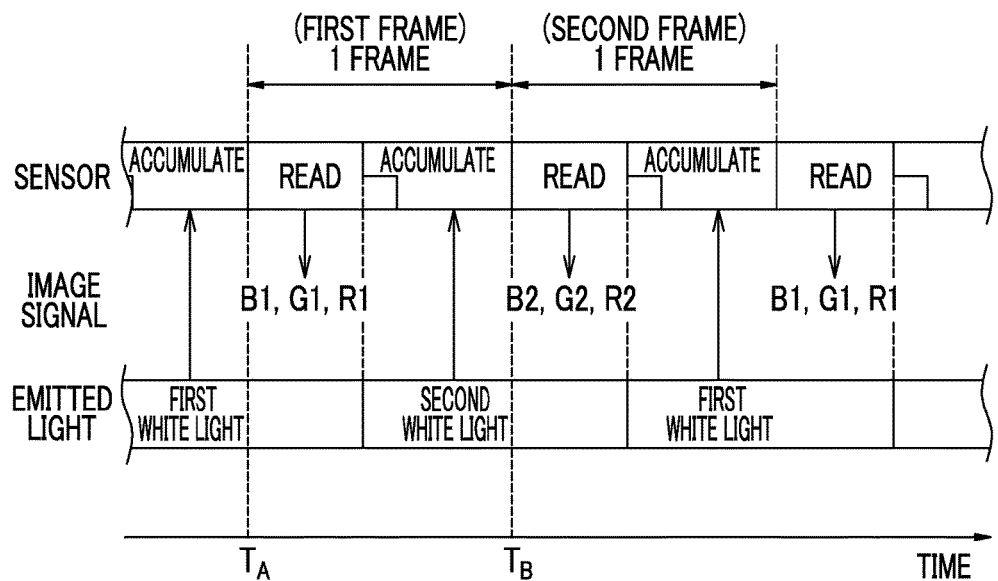
FIG. 7 is an explanatory diagram showing the imaging control in the special observation mode when a sensor is a CCD.

Also in the special observation mode, the imaging control unit 49 performs imaging control of the sensor 48 in the same manner as in the normal observation mode. However, in the special observation mode, the first white light and the second white light are alternately emitted to the observation target in synchronization with the imaging frame of the sensor 48. Therefore, as shown in FIG. 7, the sensor 48 reads signal charges, which are obtained by imaging the observation target under the first white light, in the reading period of the first frame, and outputs the image signals of RGB colors. Then, the sensor 48 reads signal charges, which are obtained by imaging the observation target under the second white light, in the reading period of the second frame, and outputs the image signals of RGB colors. The RGB image signals of two frames are used for the calculation of the oxygen saturation and the generation of an oxygen saturation image.

The sensor 48 outputs the image signals of RGB colors in both the first and second frames. However, the spectrum of white light in the first frame and the spectrum of white light in the second frame are different. Therefore, for the sake of distinction, the image signals of RGB colors that the sensor 48 outputs in the first frame are referred to as an R1 image signal, a G1 image signal, and a B1 image signal, and the image signals of RGB colors that the sensor 48 outputs in the second frame are referred to as an R2 image signal, a G2 image signal, and a B2 image signal.

As shown in FIG. 2, the image signals of the respective colors output from the sensor 48 are transmitted to a correlated double sampling (CDS)/automatic gain control (AGC) circuit 50. The CDS/AGC circuit 50 performs correlated double sampling (CDS) or automatic gain control (AGC) for the analog image signals output from the sensor 48. The image signals transmitted through the CDS/AGC circuit 50 are converted into digital image signals by an A/D converter 52. The image signals that have been digitized in this manner are input to the processor device 16.

The processor device 16 includes a receiving unit 54, a digital signal processor (DSP) 56, a noise removal unit 58, a signal conversion unit 59, an endoscope image input unit 60, a past endoscope image storage unit 61, a normal observation image processing unit 62, a special observation image processing unit 64, and an image display signal generation unit 66. The receiving unit 54 receives the image signal input from the endoscope 12.

The DSP 56 performs various kinds of signal processing, such as defect correction processing, offset processing, gain correction processing, linear matrix processing, gamma conversion processing, demosaic processing, and YC conversion processing, on the received image signal. In the defect correction processing, the signal of the defective pixel of the sensor 48 is corrected. In the offset processing, a dark current component is removed from the image signal subjected to the defect correction processing, and the exact zero level is set. In the gain correction processing, the signal level of each image signal is adjusted by multiplying each of the RGB image signals after the offset processing by a specific gain. Linear matrix processing for increasing color reproducibility is performed on the image signal of each color after the gain correction processing.

Then, the brightness or saturation of each image signal is adjusted by gamma conversion processing. Demosaic processing (also referred to as isotropic processing or synchronization processing) is performed on the image signal after the linear matrix processing, and the signal of missing color of each pixel is generated by interpolation. Although only a signal of one color of RGB is present in each pixel before demosaic processing, all pixels have signals of RGB colors through the demosaic processing. The signal conversion unit 59 performs YC conversion processing on each image signal after the demosaic processing, and outputs a brightness signal Y and color difference signals Cb and Cr to the noise removal unit 58.

The noise removal unit 58 performs noise removal processing using, for example, a moving average method or a median filter method on the image signal subjected to the demosaic processing or the like by the DSP 56. The image signals after noise has been removed are input to the signal conversion unit 59. The signal conversion unit 59 reconverts the brightness signal Y and the color difference signals Cb and Cr into RGB image signals, and inputs the RGB image signals after reconversion to the endoscope image input unit 60.

When the mode selector SW 22b is set to the normal observation mode, the image processing switching unit 60 inputs the image signals to the normal observation image processing unit 62. On the other hand, when the observation mode selector SW 22b is set to the special observation mode, the image processing switching unit 60 inputs the image signals to the special observation image processing unit 64. Here, the image signals input to the normal observation image processing unit 62 or the special observation image processing unit 64 are image signals output from the endoscope 12 that is currently inserted into the subject. Accordingly, the image signals input to the normal observation image processing unit 62 or the special observation image processing unit 64 are assumed to be current endoscope image signals. In addition, an image signal input to the special observation image processing unit 64 among the current endoscope image signals is used for the calculation of the oxygen saturation.

The past endoscope image storage unit 61 stores a past endoscope image signal that was obtained during the past endoscope insertion and is different from a signal for oxygen saturation calculation. The past endoscope image storage unit 61 outputs the past endoscope image signal to the special observation image processing unit 64 in response to the input of a simultaneous display instruction signal for simultaneous display of the current and past oxygen saturation images. The simultaneous display instruction signal is transmitted according to the operation of the console 20. Here, "during the past endoscope insertion" refers to "during the endoscope insertion in a primary examination that is performed in a clinic or a community hospital where an endoscope having an oxygen saturation measurement function is not provided", for example. On the other hand, "during the current endoscope insertion" refers to "during the endoscope insertion in a secondary examination that is performed after the primary examination in a large-scale hospital where an endoscope having an oxygen saturation measurement function is provided", for example.

The past endoscope image signals include image signals of three colors of a B (blue) past image signal, a G (green) past image signal, and an R (red) past image signal. As the past endoscope image signals, for example, not only an image signal of a normal observation image obtained by emitting white light ranging from blue to red but also an image signal of a narrowband image obtained by emitting narrowband light having a specific wavelength and an image signal of a fluorescence image obtained by receiving the auto-fluorescence or drug fluorescence can be mentioned. In addition, the past endoscope image signals are input not only to an image input and output unit (not shown) provided in the processor device 16 but also to the past endoscope image storage unit 61 through various networks, such as a LAN.

The normal observation image processing unit 62 performs color conversion processing, such as 3×3 matrix processing, gradation conversion processing, and three-dimensional LUT processing, on each of the input image signals of RGB of one frame. Not only various kinds of color enhancement processing but also structure enhancement processing, such as spatial frequency enhancement, is performed on the RGB image signals subjected to the color conversion processing. The RGB image signals subjected to the structure enhancement processing or the like are input to the image display signal generation unit 66 as a normal observation image.

The special observation image processing unit 64 generates a current oxygen saturation image based on the current endoscope image signal output from the endoscope image input unit 60, and generates a past oxygen saturation image based on the past endoscope image signal output from the past endoscope image storage unit 61. The current oxygen saturation image and the past oxygen saturation image are input to the image display signal generation unit 66.

The image display signal generation unit 66 converts the normal observation image or the current or past oxygen saturation image into a display format signal (display image signal), and inputs the display format signal to the monitor 18. The monitor 18 displays a predetermined image according to the input display format signal.

Figure 8:
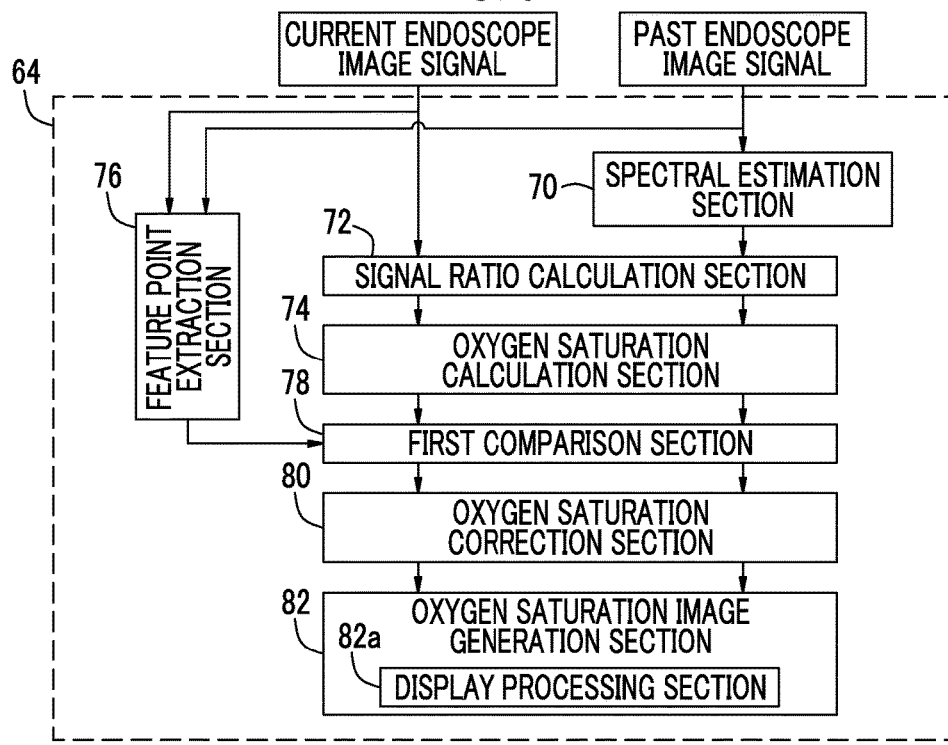
FIG. 8 is a block diagram of a special observation image processing unit of the first embodiment.

As shown in FIG. 8, the special observation image processing unit 64 includes a spectral estimation section 70, a signal ratio calculation section 72, an oxygen saturation calculation section 74, a feature point extraction section 76, a first comparison section 78, an oxygen saturation correction section 80, and an oxygen saturation image generation section 82.

A past endoscope image signal from the past endoscope image storage unit 61 is input to the spectral estimation section 70. The spectral estimation section 70 generates a spectral estimation image by performing spectral estimation processing on the past endoscope image signal. The spectral estimation image is configured to include a B spectral estimation signal corresponding to the wavelength band $\lambda b$ of the first blue laser light, a G spectral estimation signal corresponding to the wavelength band $\lambda g$ incident on the G pixel of the second white light, and an R spectral estimation signal corresponding to the wavelength band $\lambda r$ incident on the R pixel of the second white light.

The spectral estimation processing is performed by matrix processing based on the following Expression (1). Details of the spectral estimation processing are disclosed in JP2003-93336A.

$$\begin{pmatrix} Rs \\ Gs \\ Bs \end{pmatrix} = \begin{pmatrix} k12 & k12 & k13 \\ k21 & k22 & k23 \\ k31 & k32 & k32 \end{pmatrix} \begin{pmatrix} Rp \\ Gp \\ Bp \end{pmatrix} \qquad (1)$$

Here, in Expression (1), "Rp" indicates an R past image signal of the past endoscope image signal, "Gp" indicates a G past image signal of the past endoscope image signal, and "Bp" indicates a B past image signal of the past endoscope image signal. In addition, "Rs" indicates an R spectral estimation signal of the spectral estimation image, "Gs" indicates a G spectral estimation signal of the spectral estimation image, and "Bs" indicates a B spectral estimation image of the spectral estimation image. In addition, "k11, k12, k13" are matrix coefficients corresponding to the wavelength band $\lambda r$, "k21, k22, k23" are matrix coefficients corresponding to the wavelength band $\lambda g$, and "k31, k32, k33" are matrix coefficients corresponding to the wavelength band $\lambda b$.

Among the current endoscope image signals of two frames from the endoscope image input unit 60, the B1 image signal, the G2 image signal, and the R2 image signal (image signal of a specific image) are input to the signal ratio calculation section 72. In addition, the B spectral estimation signal, the G spectral estimation signal, and the R spectral estimation signal obtained by the spectral estimation section 70 are input to the signal ratio calculation section 72. The signal ratio calculation section 72 calculates a signal ratio B/G between the B1 image signal and the G2 image signal and a signal ratio R/G between the G2 image signal and the R2 image signal for each pixel. The signal ratios B/G and R/G obtained from the B1 image signal, the G2 image signal, and the R2 image signal are used for the calculation of the oxygen saturation (current oxygen saturation) of the observation target observed during the current endoscope insertion. Accordingly, the signal ratios B/G and R/G obtained from the B1 image signal, the G2 image signal, and the R2 image signal are assumed to be the signal ratios B/G and R/G for current oxygen saturation calculation.

In addition, the signal ratio calculation section 72 calculates a signal ratio B/G between the B spectral estimation signal and the G spectral estimation signal and a signal ratio R/G between the G spectral estimation signal and the R spectral estimation signals for each pixel. The signal ratios B/G and R/G obtained from the B spectral estimation signal, the G spectral estimation signal, and the R spectral estimation signal are used for the calculation of the oxygen saturation (past oxygen saturation) of the observation target observed during the past endoscope insertion. Accordingly, the signal ratios B/G and R/G obtained from the B spectral estimation signal, the G spectral estimation signal, and the R spectral estimation signal are assumed to be the signal ratios B/G and R/G for past oxygen saturation calculation.

The oxygen saturation calculation section 74 calculates the current oxygen saturation (second oxygen saturation) based on the signal ratios B/G and R/G for current oxygen saturation calculation and calculates the past oxygen saturation (first oxygen saturation) based on the signal ratios B/G and R/G for past oxygen saturation calculation. The oxygen saturation calculation section 74 stores a correlation between the signal ratios B/G and R/G and the oxygen saturation, and calculates the current oxygen saturation or the past oxygen saturation with reference to the correlation.

Figure 9:
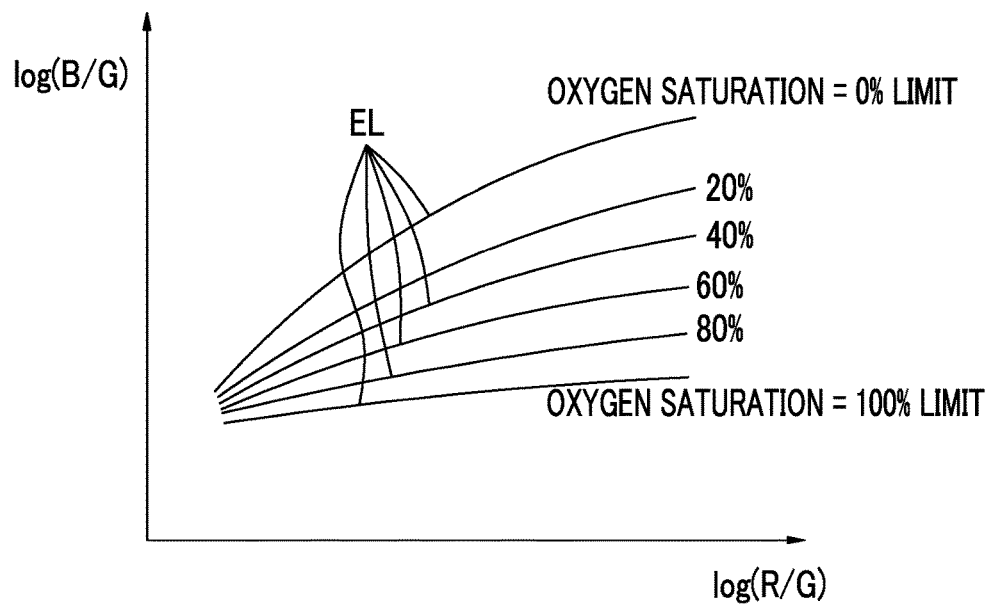
FIG. 9 is a graph showing the correlation between the signal ratio and the oxygen saturation.

For the above correlation, when the relationship between the signal ratios B/G and R/G and the oxygen saturation is expressed on two-dimensional color space (vertical axis: signal ratio B/G horizontal axis: signal ratio R/G), an isoline EL having approximately the same oxygen saturation extends along the horizontal axis direction, and the isoline EL is shifted in the positive direction of the vertical axis as the oxygen saturation becomes low, as shown in FIG. 9. In addition, the position and shape of each isoline for the signal ratios B/G and R/G are obtained in advance by physical simulation of light scattering, and the distance between isolines changes according to the signal ratio R/G (signal ratio R/G greatly changes with the blood volume). In addition, the correlation between the signal ratios B/G and R/G and the oxygen saturation is stored in a log scale.

Figure 10:
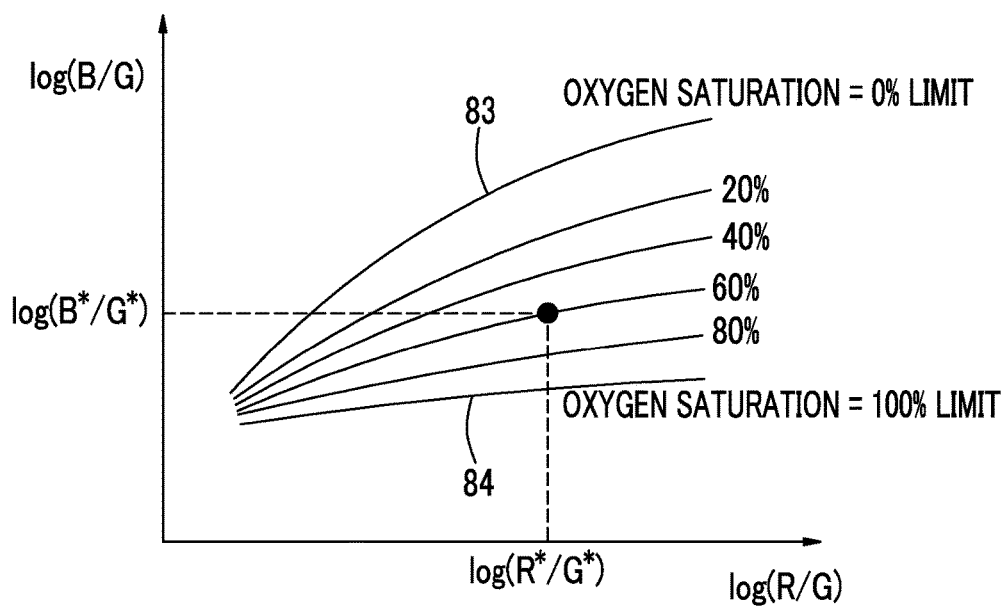
FIG. 10 is an explanatory view showing an oxygen saturation calculation method.

The oxygen saturation calculation section 74 calculates an oxygen saturation corresponding to the signal ratios B/G and R/G for current oxygen saturation calculation that have been calculated by the signal ratio calculation section 72, as the current oxygen saturation, for each pixel with reference to the above correlation stored in advance. For example, when the signal ratios B/G and R/G in a specific pixel are B*/G* and R*/G*, respectively, the oxygen saturation corresponding to the signal ratios B*/G* and R*/G* is "60%" when the correlation shown in FIG. 10 is referred to. Accordingly, the oxygen saturation calculation section 74 calculates the oxygen saturation of the pixel as "60%". In addition, the past oxygen saturation is also calculated in the same manner as the current oxygen saturation. The current or past oxygen saturation calculated by the oxygen saturation calculation section 74 is transmitted to the first comparison section 78.

In addition, a case where the signal ratios B/G and R/G become extremely large or extremely small hardly occurs. That is, a case hardly occurs in which the value of the signal ratio B/G or the signal ratio R/G exceeds a lower limit isoline 83 of the oxygen saturation of 0% or on the contrary becomes lower than an upper limit isoline 84 of the oxygen saturation of 100%. Here, the oxygen saturation calculation section 74 sets the oxygen saturation to 0% when the calculated oxygen saturation is lower than the lower limit isoline 83, and sets the oxygen saturation to 100% when the calculated oxygen saturation exceeds the upper limit isoline 84. In addition, when a point corresponding to the signal ratios B/G and R/G deviates from a region between the lower limit isoline 83 and the upper limit isoline 84, display showing that the reliability of the oxygen saturation in the pixel is low may be performed, or the oxygen saturation may not be calculated.

Figure 11:
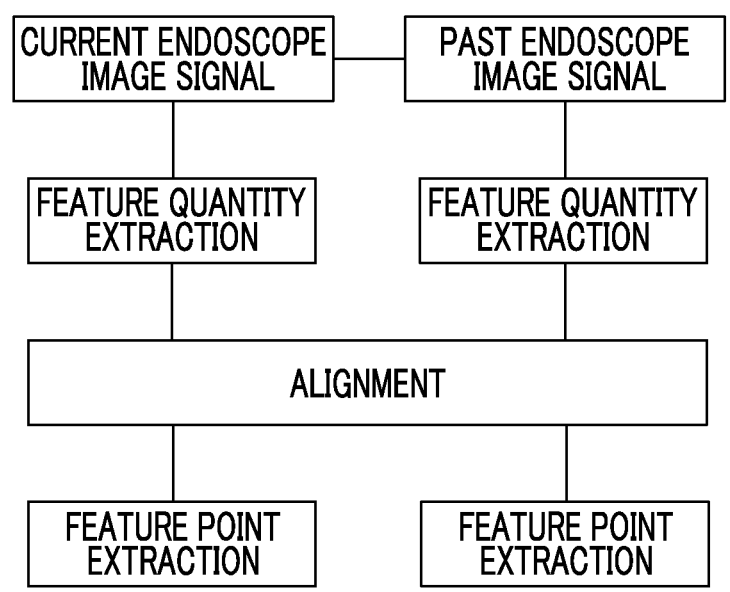
FIG. 11 is an explanatory view showing a feature point extraction method.

The feature point extraction section 76 extracts feature points having the same feature quantity (or approximately the same feature quantity) in the current endoscope image signal and the past endoscope image signal. As shown in FIG. 11, first, a feature quantity is extracted from each of the current endoscope image signal and the past endoscope image signal. Examples of the extracted feature quantity include a contrast difference between the blood vessel and the mucous membrane and the edge strength of a blood vessel running pattern. Then, the alignment of the current endoscope image signal and the past endoscope image signal is performed such that the feature quantities match between the current endoscope image signal and the past endoscope image signal. Then, between the current endoscope image signal and the past endoscope image signal after the alignment, pixel regions having the same or approximately the same feature quantity are extracted as feature points. Information regarding the feature points of the current and past endoscope image signals is transmitted to the first comparison section 78. In addition to automatically extracting the feature point by the feature point extraction section 76, the feature point may be extracted in response to the instruction of the user (for example, a doctor who is a user may extract a region of interest as a feature point by operating the console 20).

The first comparison section 78 compares the oxygen saturation of a first feature point having a specific feature quantity among the feature points on the current endoscope image signal with the oxygen saturation of a second feature point having the same feature quantity as the first feature point among the feature points on the past endoscope image signal. The first comparison section 78 performs the above comparison based on the difference between the oxygen saturation of the first feature point and the oxygen saturation of the second feature point (difference in oxygen saturation between the feature points). Information regarding the difference in oxygen saturation between the feature points and information regarding the current and past oxygen saturations in each pixel are transmitted to the oxygen saturation correction section 80. In addition to comparing the oxygen saturation of the first feature point with the oxygen saturation of the second feature point, the oxygen saturation in a first region surrounded by a plurality of feature points in the current endoscope image signal may be compared with the oxygen saturation in a second region corresponding to the first region in the past endoscope image signal, or the oxygen saturation in a peripheral region of the first feature point may be compared with the oxygen saturation in a peripheral region of the second feature point.

Based on the difference between the oxygen saturations of the feature points of the current and past endoscope image signals, the oxygen saturation correction section 80 performs correction so that the difference between the current oxygen saturation and the past oxygen saturation in each pixel is eliminated. For example, when the difference in oxygen saturation between the feature points is calculated by subtracting the oxygen saturation of the second feature point from the oxygen saturation of the first feature point, if the difference in oxygen saturation between the feature points is "+5%", shift processing for oxygen saturation correction for subtracting "+5%" from the current oxygen saturation or shift processing for adding "+5%" to the past oxygen saturation is performed for each pixel. Other than the shift processing, the correction may be realized by performing gain processing for oxygen saturation correction, which is processing for multiplying the current or past oxygen saturation by the gain factor for oxygen saturation correction corresponding to the oxygen saturation between feature points, for each pixel. In addition, the correction of the current or past oxygen saturation may be repeatedly performed until the difference between the current oxygen saturation and the past oxygen saturation is eliminated (becomes approximately "0"). In addition, the oxygen saturation correction section 80 may correct the current oxygen saturation and the past oxygen saturation by combining the shift processing and the gain processing for oxygen saturation correction.

The oxygen saturation image generation section 82 includes a display processing section 82a. The display processing section 82a generates a current oxygen saturation image (second oxygen saturation image) by imaging the current oxygen saturation by performing display processing, which is for displaying a specific range and a range outside the specific range in different display methods, the current oxygen saturation after correction in the specific range being set in advance. In addition, the display processing section 82a generates a past oxygen saturation image (first oxygen saturation image) by imaging the past oxygen saturation by performing display processing, which is for displaying a specific range and a range outside the specific range in different display methods, the current oxygen saturation after correction in the specific range being set in advance.

As the display processing on the current endoscope image signal, the display processing section 82a multiplies a B2 image signal, a G2 image signal, and an R2 image signal of the current endoscope image signals by a coefficient for image generation, which corresponds to the current oxygen saturation after correction, for each pixel. Here, in a pixel within the specific range where the current oxygen saturation is 60% or more of the boundary value, all of the B2 image signal, the G2 image signal, and the R2 image signal are multiplied by the same color adjustment coefficient "1". In contrast, in a pixel outside the specific range where the current oxygen saturation is less than 60% of the boundary value, the B2 image signal is multiplied by the color adjustment coefficient less than "1", and the G2 image signal and the R2 image signal are multiplied by the color adjustment coefficient exceeding "1". Through the multiplication of such a color adjustment coefficient, a high-oxygen region within the specific range where the oxygen saturation is 60% to 100% is expressed by the same color as the image based on the current endoscope image signal. On the other hand, a low-oxygen region outside the specific range where the oxygen saturation is 0% to 60% is expressed by a different color (pseudo-color) from the image based on the current endoscope image signal. Therefore, the low-oxygen region outside the specific range is displayed in a display method different from the high-oxygen region within the specific range.

In addition, as the display processing on the past endoscope image signal, the display processing section 82a multiplies a B past image signal, a G past image signal, and an R past image signal of the past endoscope image signals by a color adjustment coefficient, which corresponds to the past oxygen saturation after correction, for each pixel. Others are generated in the same manner as the current oxygen saturation image described above. Although the oxygen saturation image generation section 82 performs the multiplication of such a color adjustment coefficient for pseudo-coloring only for the low-oxygen region in the present embodiment, a color adjustment coefficient corresponding to the oxygen saturation may also be multiplied for the high-oxygen region so that the entire oxygen saturation image is pseudo-colored.

Figure 12:
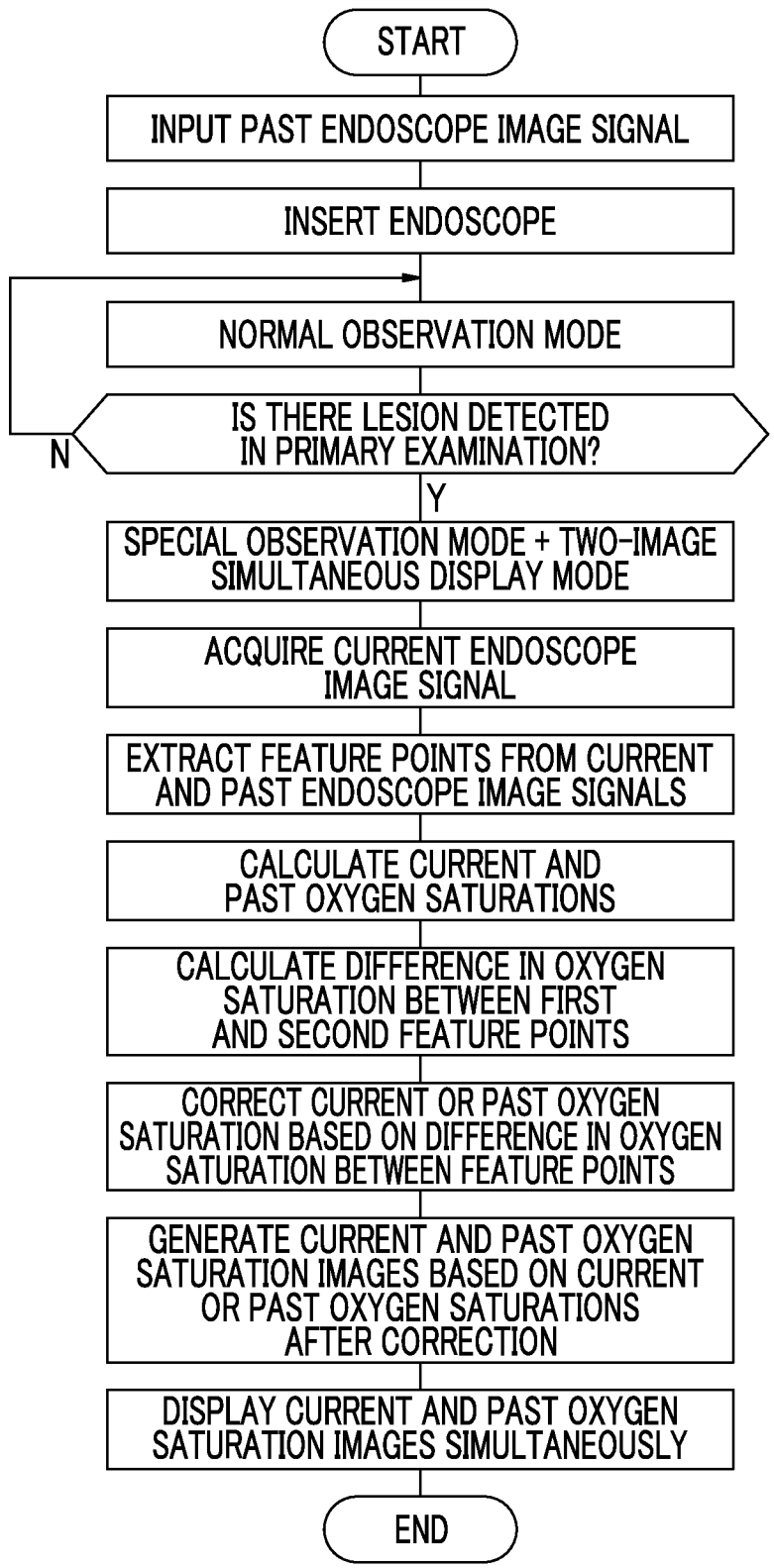
FIG. 12 is a flowchart showing a series of flow in the first embodiment.

Next, the flow of observation using the endoscope system 10 according to the present embodiment will be described with reference to the flowchart in FIG. 12. First, before starting the endoscopic diagnosis, a past endoscope image signal obtained in the previous primary examination is input to the past endoscope image storage unit 61. Then, the endoscope 12 is inserted into the subject, and screening is performed from the most distant view state in the normal observation mode. In the normal observation mode, a normal observation image that is the current image is displayed on the monitor 18. When a lesion detected in the primary examination is found during the screening, switching to the special observation mode is performed by operating the mode selector SW 22b, and a two-image simultaneous display mode is set by operating the console 20 in order to observe the progress of the lesion.

In the special observation mode, the first and second white light beams are alternately emitted to the observation target in units of a frame. Accordingly, the sensor 48 outputs the R1 image signal, the G1 image signal, and the B1 image signal in a frame in which the first white light is emitted, and outputs the R2 image signal, the G2 image signal, and the B2 image signal in a frame in which the second white light is emitted. As a result, a current endoscope image signal including the image signals B1, G1, R1, B2, G2, and R2 of two frames is obtained. The current endoscope image signal is transmitted to the special observation image processing unit 64. On the other hand, a past endoscope image signal including the B past image signal, the G past image signal, and the R past image signal is transmitted to the special observation image processing unit 64 from the past endoscope image storage unit 61.

In the special observation image processing unit 64, the feature point extraction section 76 performs alignment between the current endoscope image signal and the past endoscope image signal based on the feature quantity, such as a contrast difference between the blood vessel and the mucous membrane, and extracts a plurality of feature points from the current endoscope image signal and the past endoscope image signal after the alignment. Then, the spectral estimation section 70 generates a spectral estimation image including the B spectral estimation signal, the G spectral estimation signal, and the R spectral estimation signal by performing spectral estimation processing on the past endoscope image signal. Then, the signal ratio calculation section 72 calculates the signal ratios B/G and R/G for current oxygen saturation calculation, for each pixel, based on the B1 image signal, the G2 image signal, and the R2 image signal among the current endoscope image signals, and calculates the signal ratios B/G and R/G for past oxygen saturation calculation, for each pixel, based on the B spectral estimation signal, the G spectral estimation signal, and the R spectral estimation signal of the spectral estimation image.

Then, the oxygen saturation calculation section 74 calculates the current oxygen saturation for each pixel based on the signal ratios B1/G2 and R2/G2 for current oxygen saturation calculation, and calculates the past oxygen saturation for each pixel based on the signal ratios B1/G2 and R2/G2 for past oxygen saturation calculation.

Then, the first comparison section 78 calculates a difference between the oxygen saturation of the first feature point having a specific feature quantity among the feature points on the current endoscope image signal and the oxygen saturation of the second feature point having the same feature quantity as the first feature point among the feature points on the past endoscope image signal. Information regarding the difference between the oxygen saturation of the first feature point and the oxygen saturation of the second feature point is transmitted to the oxygen saturation correction section 80. Then, based on the difference between the oxygen saturations of the feature points of the current and past endoscope image signals, the oxygen saturation correction section 80 performs correction so that the difference between the current oxygen saturation and the past oxygen saturation in each pixel is eliminated.

Figure 13:
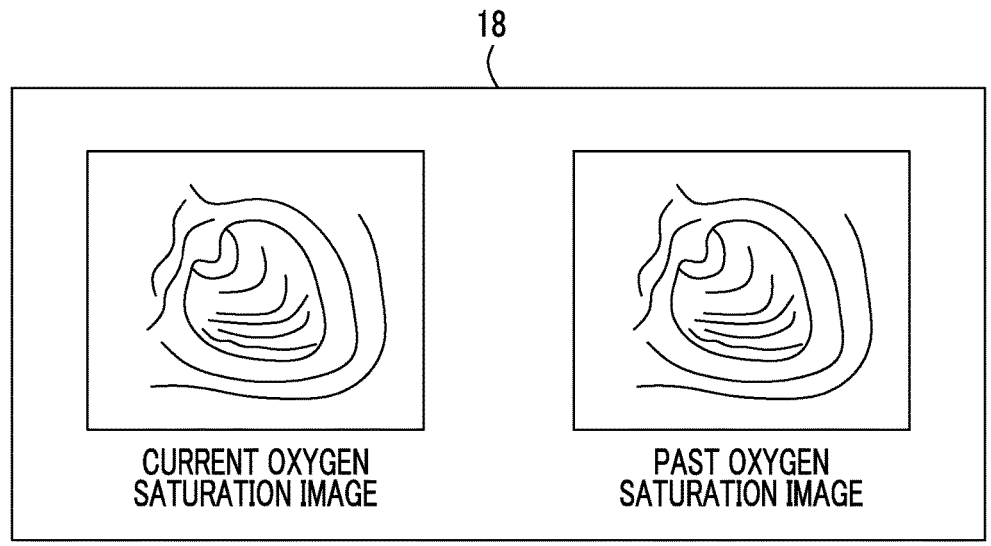
FIG. 13 is a diagram showing an image on a monitor in which a current oxygen saturation image and a past oxygen saturation image are simultaneously displayed.

Then, the oxygen saturation image generation section 82 generates a current oxygen saturation image by imaging the current oxygen saturation using the current oxygen saturation and the current endoscope image signal after the correction, and generates a past oxygen saturation image using the past oxygen saturation and the past endoscope image signal after the correction. The current oxygen saturation image and the past oxygen saturation image that have been generated are simultaneously displayed on the monitor 18, as shown in FIG. 13.

As described above, in the invention, the current oxygen saturation image and the past oxygen saturation image are simultaneously displayed. Therefore, since it is possible to compare and analyze an oxygen state change in the lesion based on the colors, it is possible to reliably observe the progress of the lesion. In addition, even if the past image is not an oxygen saturation image, such as a normal observation image, it is possible to generate a past oxygen saturation image c by using the spectral estimation processing.

In the spectral estimation processing, a difference in estimation accuracy may occur due to individual differences or part differences, and a difference between the current oxygen saturation and the past oxygen saturation may occur due to the difference in estimation accuracy. In such a case, a difference may occur between the display of the current oxygen saturation image and the display of the past oxygen saturation image. On the other hand, in the invention, the oxygen saturation correction section 80 performs correction so that the difference between the current oxygen saturation and the past oxygen saturation in each pixel is eliminated. Therefore, even if a difference in estimation accuracy of the spectral estimation processing occurs due to individual differences or the like, a difference between the display of the current oxygen saturation image and the display of the past oxygen saturation image due to the difference in estimation accuracy does not occur.

Second Embodiment

In an endoscope system of a second embodiment, a matrix coefficient used in the spectral estimation processing is corrected according to the difference between the current oxygen saturation and the past oxygen saturation, instead of correcting the current oxygen saturation and the past oxygen saturation using the oxygen saturation correction section. Others are approximately the same as in the first embodiment.

Figure 14:
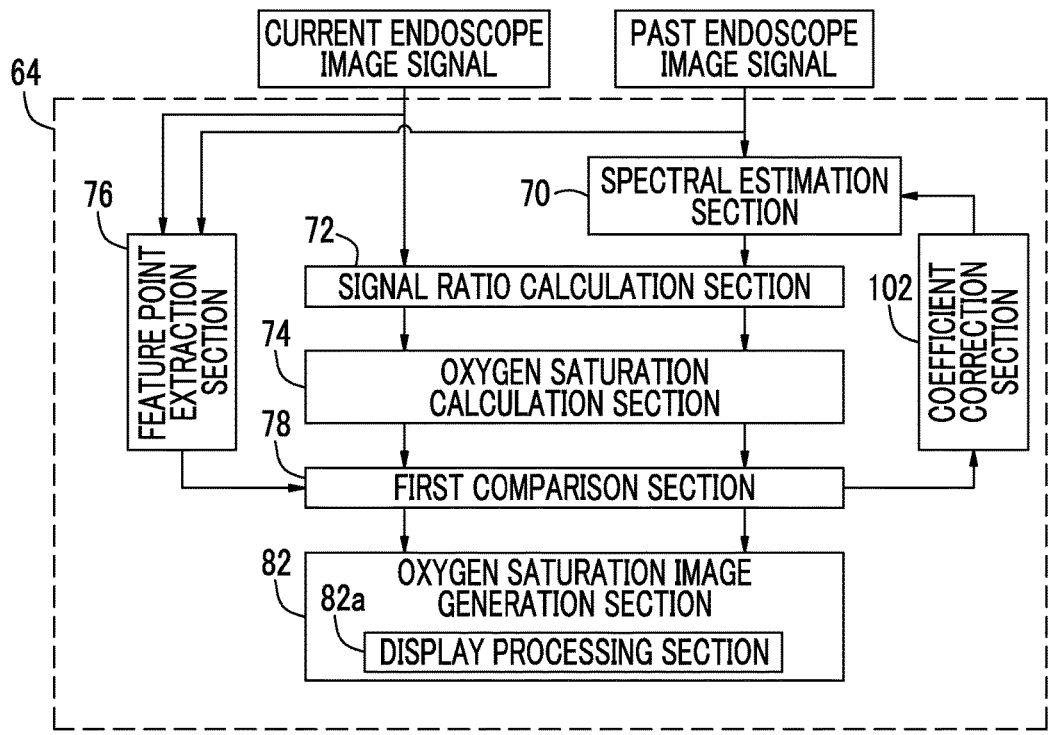
FIG. 14 is a block diagram of a special observation image processing unit of a second embodiment.

As shown in FIG. 14, a special observation image processing unit 100 of the second embodiment includes a spectral estimation section 70, a signal ratio calculation section 72, an oxygen saturation calculation section 74, a feature point extraction section 76, a first comparison section 78, a coefficient correction section 102, and an oxygen saturation image generation section 82. Compared with the special observation image processing unit 64 of the first embodiment, the special observation image processing unit 100 of the second embodiment includes the newly added coefficient correction section 102 instead of the oxygen saturation correction section 80 being removed.

The coefficient correction section 102 corrects matrix coefficients k11, k12, k13, k21, k22, k23, k31, k32, and k33 used in the spectral estimation section 70 based on the difference in oxygen saturation between the feature points of the current and past endoscope image signals calculated by the first comparison section 78. The coefficient correction section 102 stores the relationship between the correction coefficient for correcting the matrix coefficient and the difference in oxygen saturation between the feature points in advance, and corrects the matrix coefficient using the relationship. Based on the matrix coefficient after the correction, the spectral estimation processing is performed again by the spectral estimation section 70. Then, the signal ratio calculation section 72 re-calculates the signal ratios B/G and R/G for past oxygen saturation based on the spectral estimation image after the spectral estimation processing is performed again, and the oxygen saturation calculation section 74 re-calculates the past oxygen saturation based on the signal ratios B/G and R/G for past oxygen saturation calculation.

As described above, by correcting the matrix coefficient according to the difference in oxygen saturation between the first and second feature points and calculating the oxygen saturation again after correction, it is possible to eliminate the difference between the current oxygen saturation and the past oxygen saturation in each pixel. Therefore, even if a difference in estimation accuracy of the spectral estimation processing occurs due to individual differences or the like, a difference between the display of the current oxygen saturation image and the display of the past oxygen saturation image due to the difference in estimation accuracy does not occur.

Third Embodiment

In an endoscope system of a third embodiment, the distribution of the current oxygen saturation is compared with the distribution of the past oxygen saturation instead of comparing the current oxygen saturation with the past oxygen saturation based on the difference in oxygen saturation between the first and second feature points. Others are the same as in the first embodiment.

Figure 15:
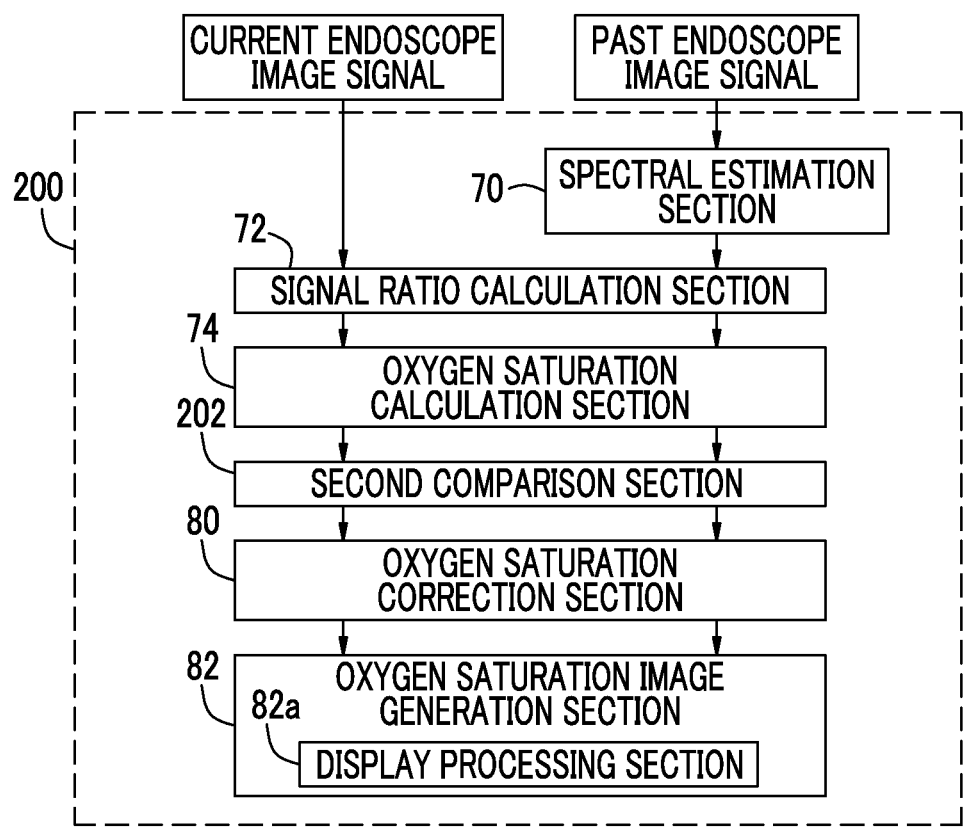
FIG. 15 is a block diagram of a special observation image processing unit of a third embodiment.

As shown in FIG. 15, a special observation image processing unit 200 of the third embodiment includes a spectral estimation section 70, a signal ratio calculation section 72, an oxygen saturation calculation section 74, a second comparison section 202, an oxygen saturation correction section 80, and an oxygen saturation image generation section 82. Compared with the special observation image processing unit 64 of the first embodiment, the special observation image processing unit 200 of the third embodiment does not include the feature point extraction section 76 and includes the newly added second comparison section 202 instead of the first comparison section 78. In addition, in the special observation image processing unit 100 of the second embodiment, the feature point extraction section 76 may be eliminated, and the second comparison section 202 may be provided instead of the first comparison section 78.

The second comparison section 202 calculates the distribution of the current oxygen saturation from the current oxygen saturations of all pixels, and calculates the distribution of the past oxygen saturation from the past oxygen saturations of all pixels. Then, the second comparison section 202 compares the distribution of the current oxygen saturation with the distribution of the past oxygen saturation, and transmits information regarding the comparison result to the oxygen saturation correction section 80. The oxygen saturation correction section 80 corrects the current or past oxygen saturation for each pixel so that the distribution of the current oxygen saturation and the distribution of the past oxygen saturation match each other.

In the above explanation, the second comparison section 202 automatically compares the distribution of the current oxygen saturation with the distribution of the past oxygen saturation. In general, however, the distribution of the current oxygen saturation may be compared with the distribution of the past oxygen saturation only when a user operates the second comparison section 202 by operating the console 20, without the second comparison section 202 comparing the distribution of the current oxygen saturation with the distribution of the past oxygen saturation.

As the information regarding the distribution of the oxygen saturation, it is possible to use a histogram showing the frequency of the oxygen saturation of 10%, the frequency of the oxygen saturation of 20%, . . . , the frequency of the oxygen saturation of 90%, and the frequency of the oxygen saturation of 100%. In this case, a histogram calculation value obtained by performing a comparison operation between the histogram regarding the current oxygen saturation and the histogram regarding the past oxygen saturation is transmitted to the oxygen saturation correction section 80. The oxygen saturation correction section 80 corrects the current or past oxygen saturation for each pixel based on the histogram calculation value. In addition, as the information regarding the distribution of the oxygen saturation, there are various statistical values, such as a maximum value, a minimum value, an average value, and a median. In this case, a statistical calculation value obtained by an operation based on various statistical values obtained from the current oxygen saturation and various statistical values obtained from the past oxygen saturation is transmitted to the oxygen saturation correction section 80. The oxygen saturation correction section 80 corrects the current or past oxygen saturation for each pixel based on the statistical calculation value.

Modifications of the First to Third Embodiments

Figure 16:
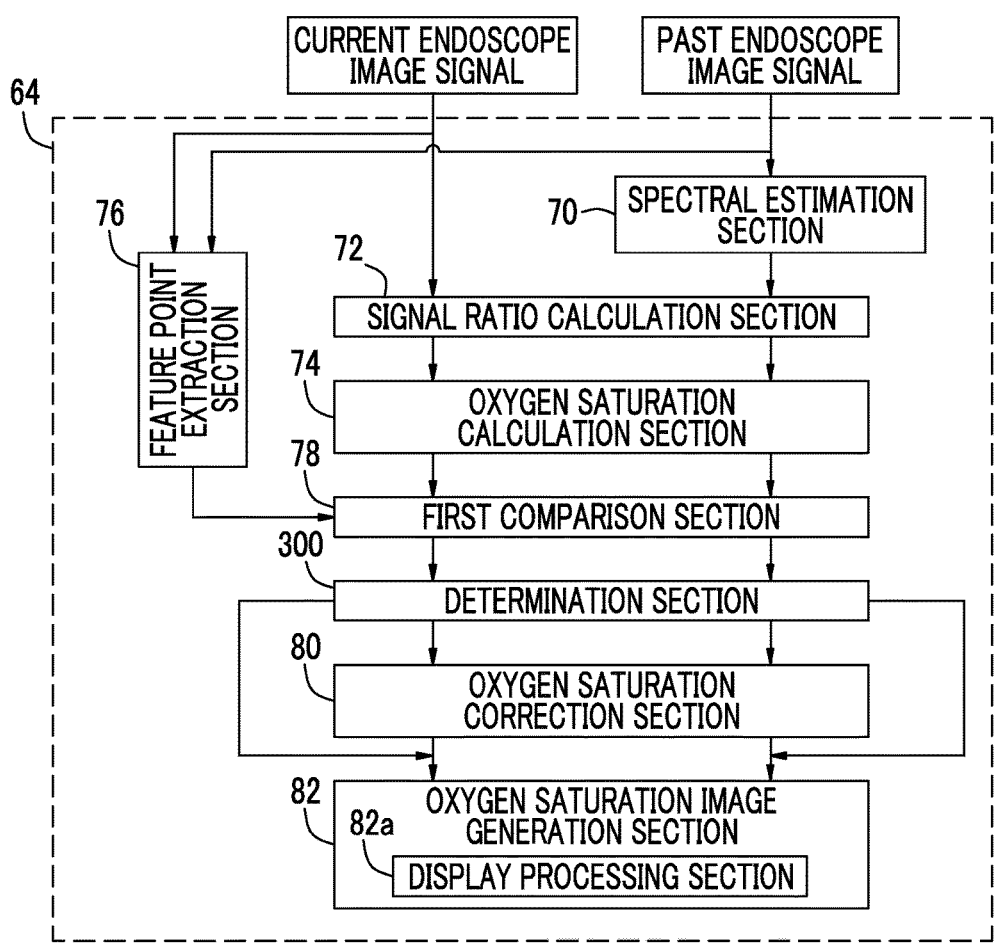
FIG. 16 is a block diagram of a special observation image processing unit in a modification of the first to third embodiments.

In the first and third embodiments, the oxygen saturation correction section 80 corrects the oxygen saturation based on the comparison result between the current oxygen saturation and the past oxygen saturation in the first comparison section 78 or the second comparison section 202. However, as shown in FIG. 16, a determination section 300 may be provided between the first comparison section 78 (in the third embodiment, the second comparison section 202) and the oxygen saturation correction section 80, and the determination section 300 may determine whether or not to correct the current or past oxygen saturation based on the comparison result between the current oxygen saturation and the past oxygen saturation.

When the determination section 300 determines that the current or past oxygen saturation is to be corrected, the comparison result of the first comparison section 78 (in the third embodiment, the second comparison section 202) and the information regarding the current or past oxygen saturation are transmitted to the oxygen saturation correction section 80. On the other hand, when the determination section 300 determines that the current or past oxygen saturation does not need to be corrected, the information regarding the current or past oxygen saturation is transmitted to the oxygen saturation image generation section 82. In addition, in the second embodiment, it is preferable to determine whether or not to correct a matrix coefficient in the coefficient correction section 102 based on the comparison result between the current oxygen saturation and the past oxygen saturation in the first comparison section 78.

Fourth Embodiment

In the first and third embodiments, the oxygen saturation correction section 80 corrects the oxygen saturation based on the comparison result between the current oxygen saturation and the past oxygen saturation in the first comparison section 78 or the second comparison section 202. In a fourth embodiment, however, the content of the display processing of the display processing section 82a is changed without correcting the oxygen saturation.

Figure 17:
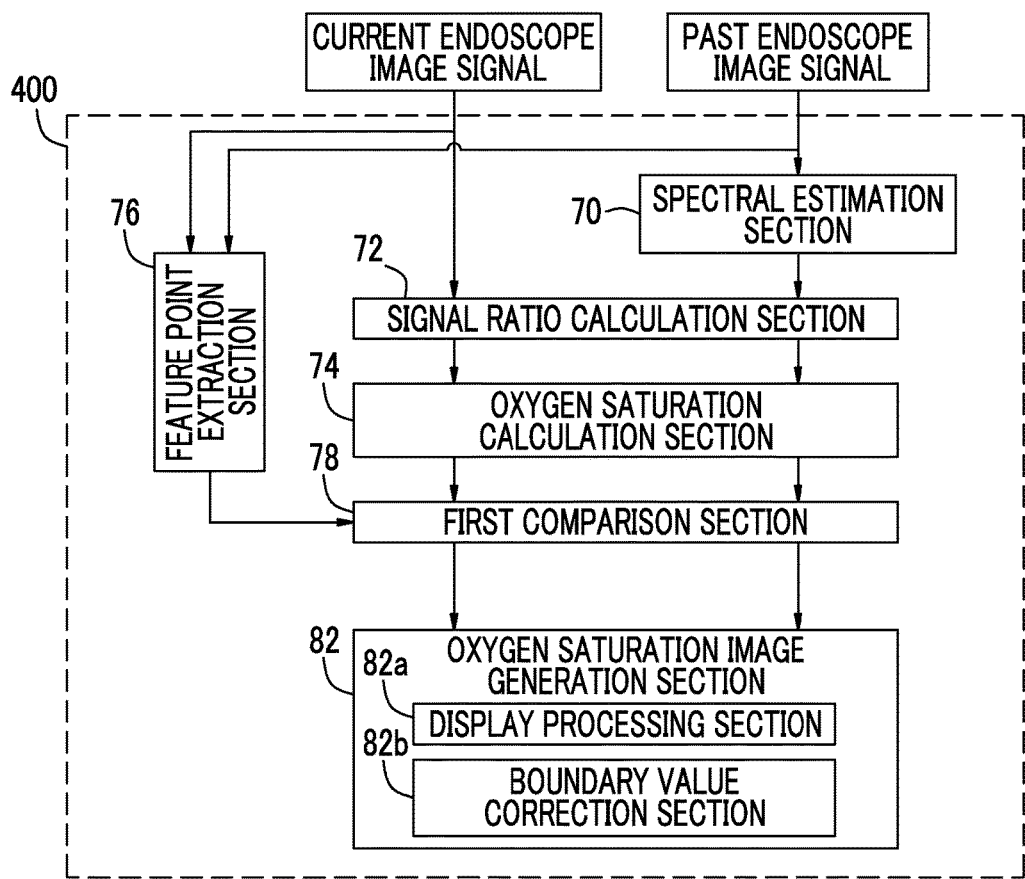
FIG. 17 is a block diagram of a special observation image processing unit of a fourth embodiment.

As shown in FIG. 17, a special observation image processing unit 400 of the fourth embodiment includes a spectral estimation section 70, a signal ratio calculation section 72, an oxygen saturation calculation section 74, a feature point extraction section 76, a first comparison section 78, and an oxygen saturation image generation section 82. Compared with the special observation image processing unit 64 of the first embodiment, in the special observation image processing unit 400 of the fourth embodiment, a boundary value correction section 82b is newly added in the oxygen saturation image generation section 82 instead of the oxygen saturation correction section 80 being removed. Others are the same as in the first embodiment.

The boundary value correction section 82b corrects the boundary value of the specific range defined by the display processing section 82a according to the difference between the oxygen saturation of the first feature point and the oxygen saturation of the second feature point. For example, when the difference in oxygen saturation between the feature points is calculated by subtracting the oxygen saturation of the second feature point from the oxygen saturation of the first feature point, if the difference in oxygen saturation between the feature points is "+5%", the boundary value of the current oxygen saturation is corrected to "55%" by subtracting "5%" from "60%" or the boundary value of the past oxygen saturation is corrected to "65%" by adding "5%" to "60%". Then, the display processing section 82a performs display processing on the current endoscope image signal and the past endoscope image signal based on the corrected boundary value. By performing display processing based on the corrected boundary value as described above, even if there is a difference in oxygen saturation between the current and past feature points, a difference between the display of the current oxygen saturation image and the display of the past oxygen saturation image due to the difference does not occur.

Fifth Embodiment

In the first to fourth embodiments, the current and past oxygen saturation images are simultaneously displayed using the current and past endoscope image signals. Instead, in the fifth embodiment, a first past oxygen saturation image and a second past oxygen saturation image are simultaneously displayed on the monitor 18 using a normal observation image obtained during the endoscope insertion in the first past and a second past oxygen saturation numerical image obtained during the endoscope insertion in the second past different from the first past. Here, the second past oxygen saturation numerical image is an image having numerical information of the second past oxygen saturation (second oxygen saturation) for each pixel.

Figure 18:
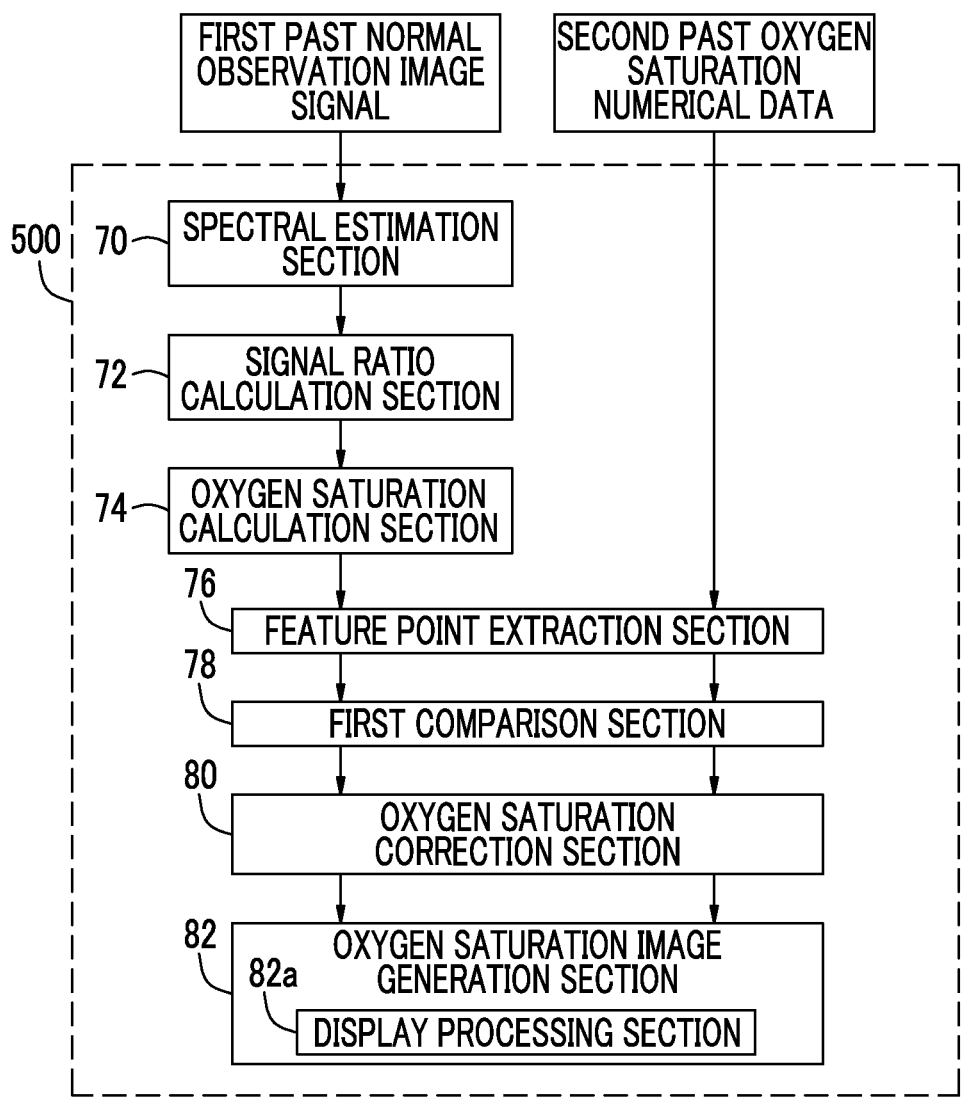
FIG. 18 is a block diagram of a special observation image processing unit of a fifth embodiment.

As shown in FIG. 18, a special observation image processing unit 500 of the fifth embodiment includes a spectral estimation section 70, a signal ratio calculation section 72, an oxygen saturation calculation section 74, a feature point extraction section 76, a first comparison section 78, an oxygen saturation correction section 80, and an oxygen saturation image generation section 82. Compared with the special observation image processing unit 64 of the first embodiment, in the special observation image processing unit 500 of the fifth embodiment, the feature point extraction section 76 is provided between the oxygen saturation calculation section 74 and the first comparison section 78. In addition, the second past oxygen saturation numerical image is input to the feature point extraction section 76 without passing through the signal ratio calculation section 72 and the oxygen saturation calculation section 74 because the second past oxygen saturation numerical image is an image having numerical information of the second past oxygen saturation. Others are the same as in the first embodiment.

Here, the first past normal observation image is an image signal obtained using broadband light, such as white light, and is stored in the past endoscope image storage unit 61. In addition, the second past oxygen saturation numerical image is an image having numerical information of the oxygen saturation for each pixel, unlike the oxygen saturation image expressing the oxygen saturation with different colors in the first to fourth embodiments. Accordingly, the second past oxygen saturation numerical image can be corrected by the oxygen saturation correction section 80. The second past oxygen saturation image is also stored in the past endoscope image storage unit 61.

When there is no correction using the oxygen saturation correction section 80, not the second past oxygen saturation numerical data but the second past oxygen saturation image expressing the oxygen saturation with different colors in the first to fourth embodiments may be stored in the past endoscope image storage unit 61. In this case, the second past oxygen saturation image is directly displayed on the monitor 18 together with the first oxygen saturation image, without each process being performed by the feature point extraction section 76, the first comparison section 78, the oxygen saturation correction section 80, and the oxygen saturation image generation section 82.

In the special observation image processing unit 500, the first past normal observation image passes through the processing of the spectral estimation section 70, the signal ratio calculation section 72, and the oxygen saturation calculation section 74 (the content of processing in each section is the same as in the first embodiment). Accordingly, the first past oxygen saturation (first oxygen saturation) is obtained. On the other hand, the second past oxygen saturation numerical image is directly input to the feature point extraction section 76 as described above. The feature point extraction section 76 extracts the feature quantity from each of the first past normal observation image and the second past oxygen saturation numerical image, and the alignment between the first past normal observation image and the second past oxygen saturation numerical image is performed based on the extracted feature quantity.

Then, from the first past normal observation image and the second past oxygen saturation numerical image after the alignment, pixel regions having the same or approximately the same feature quantity are extracted as feature points. After the feature point extraction, the same processing (each processing in the first comparison section 78, the oxygen saturation correction section 80, and the oxygen saturation image generation section 82) as in the first embodiment is performed on the first past normal observation image and the second past oxygen saturation numerical image. As a result, the first past oxygen saturation image (first oxygen saturation image) and the second past oxygen saturation image (second oxygen saturation image) are generated.

Figure 19:
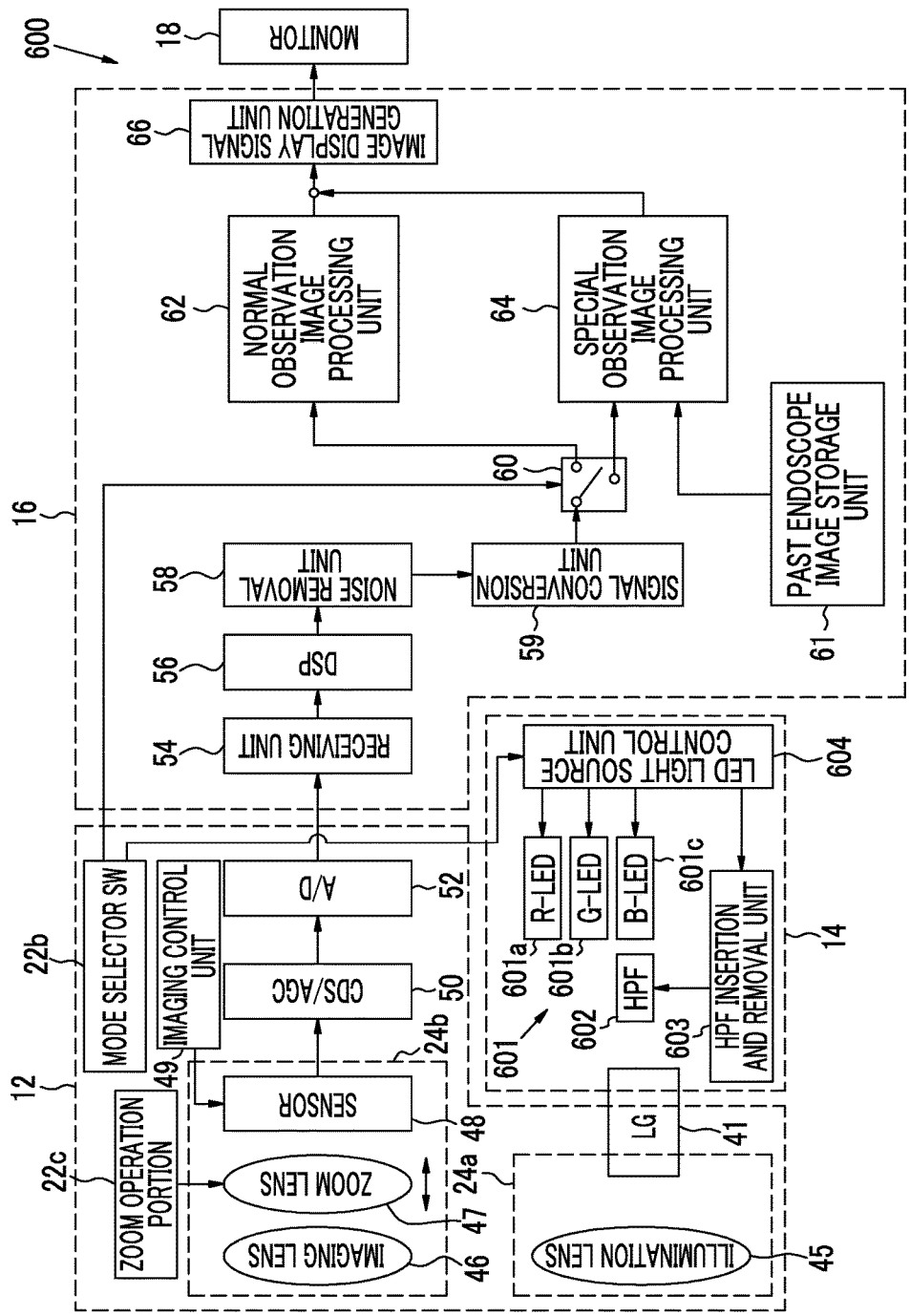
FIG. 19 is a block diagram of an LED type endoscope system.

Although the observation target is illuminated by using the first blue laser light source, the second blue laser light source, and the phosphor 44 in the first to fifth embodiments, illumination using other types of light sources is also possible. As shown in FIG. 19, in a light source device 14 of an LED type endoscope system 600, a light emitting diode (LED) light source unit 601 and an LED light LED light source control unit 604 are provided instead of the first and second blue laser light sources 34 and 36 and the light source control unit 40. In addition, the phosphor 44 is not provided in an illumination optical system 24a of an endoscope system 600. Other than these, the endoscope system 500 is the same as the endoscope system 10 according to the first embodiment.

Figure 20:
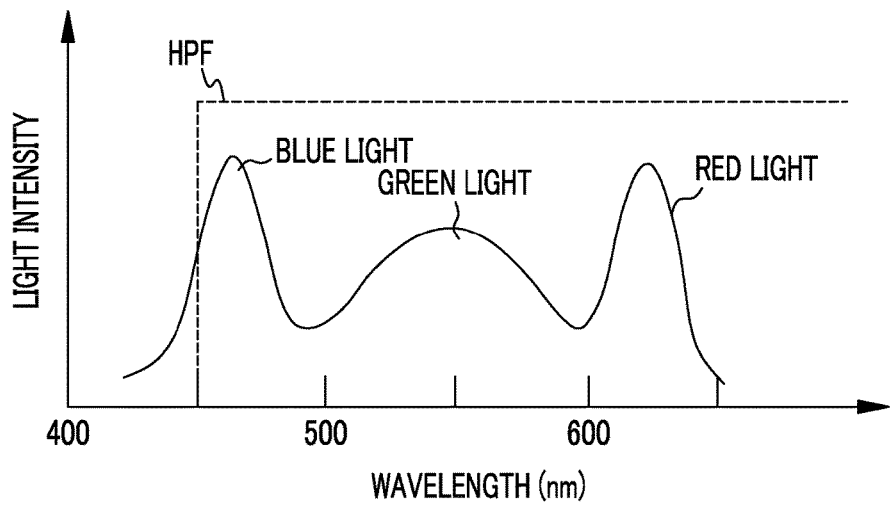
FIG. 20 is a graph showing the light emission band of an LED and the characteristics of an HPF.

The LED light source unit 601 includes an R-LED 601a, a G-LED 601b, and a B-LED 601c as light sources for emitting light limited to a specific wavelength band. As shown in FIG. 20, the R-LED 601a emits red band light (hereinafter, simply referred to as red light) having a wavelength of about 600 nm to 650 nm, for example. The center wavelength of the red light is about 620 nm to 630 nm. The G-LED 601b emits green band light (hereinafter, simply referred to as green light) having a wavelength of about 500 nm to 600 nm that is expressed by the normal distribution. The B-LED 601c emits blue band light (hereinafter, simply referred to as blue light) having a center wavelength of 445 nm to 460 nm.

In addition, the LED light source unit 601 includes a high pass filter (HPF) 602 that is removably inserted on the optical path of the blue light emitted from the B-LED 601c. The high pass filter 602 cuts the blue light having a wavelength in a wavelength band of about 450 nm or less, and allows light having a wavelength in a wavelength band higher than about 450 nm to be transmitted therethrough.

The cutoff wavelength (about 450 nm) of the high pass filter 602 is a wavelength at which the light absorption coefficient of oxygenated hemoglobin and the light absorption coefficient of reduced hemoglobin are almost equal, and the light absorption coefficient of oxygenated hemoglobin and the light absorption coefficient of reduced hemoglobin are reversed in the order of magnitude with the cutoff wavelength as a boundary. In the present embodiment, the correlation between the signal ratios B/G and R/G and the oxygen saturation is that the light absorption coefficient of oxygenated hemoglobin is larger than the light absorption coefficient of reduced hemoglobin. Accordingly, a signal based on the wavelength band equal to or lower than the cutoff wavelength is a cause of reducing the calculation accuracy of the oxygen saturation. Therefore, by preventing light having a wavelength in a wavelength band equal to or lower than the cutoff wavelength from being emitted to the observation target using the high pass filter 602 when acquiring at least the B1 image signal for calculating the oxygen saturation, the calculation accuracy of the oxygen saturation is improved.

Accordingly, the high pass filter 602 is inserted at the insertion position before the B-LED 601c in the special observation mode, and is retracted to the retraction position in the normal observation mode. The insertion and removal of the high pass filter 602 are performed by an HPF insertion and removal unit 603 under the control of the LED light source control unit 604.

Figure 21:
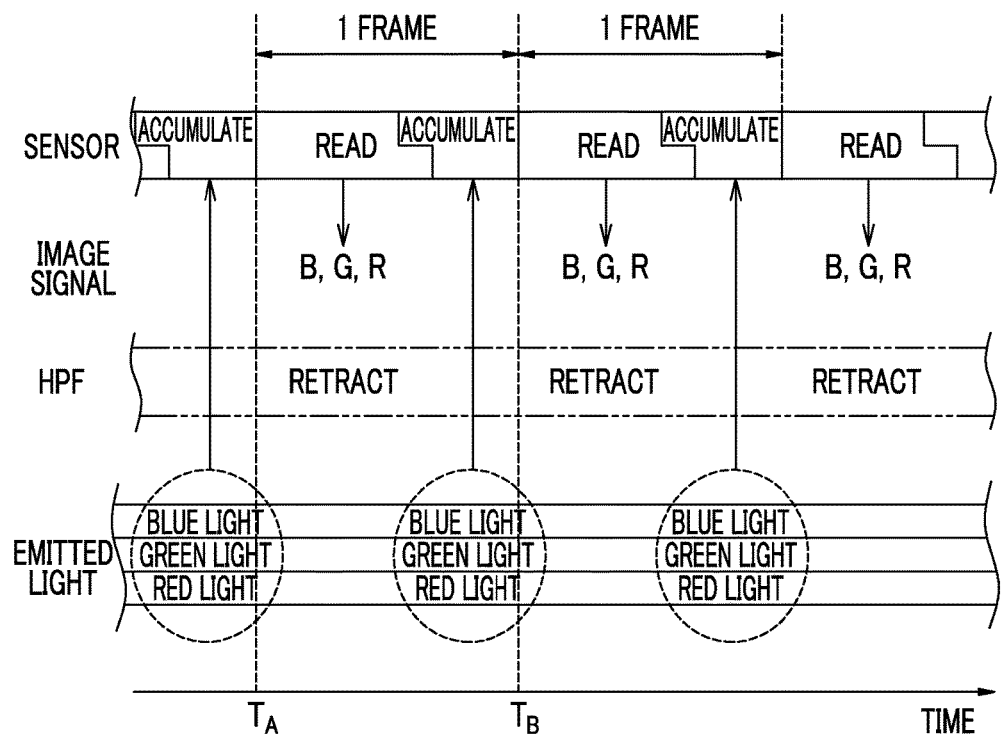
FIG. 21 is an explanatory diagram showing the imaging control in the normal observation mode in the LED type endoscope system.

The LED light source control unit 604 controls ON/OFF of the LEDs 601a to 601c of the LED light source unit 601 and the insertion and removal of the high pass filter 602. Specifically, as shown in FIG. 21, in the normal observation mode, the LED light source control unit 604 turns on all of the LEDs 601a to 601c and retracts the high pass filter 602 from the optical path of the B-LED 601c. Accordingly, white light in which blue light, green light, and red light are superimposed are emitted to the observation target, and the sensor 48 images the observation target with reflected light of the white light and outputs an image signal of each color of B, and R.

Figure 22:
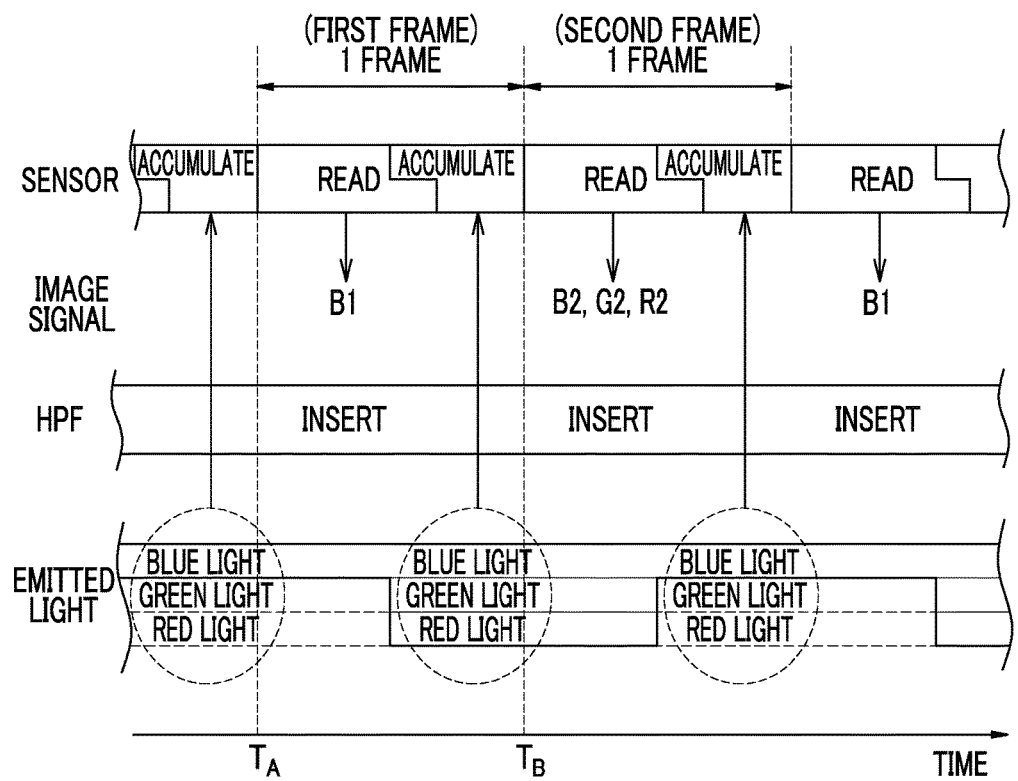
FIG. 22 is an explanatory diagram showing the imaging control in the special observation mode in the LED type endoscope system.

On the other hand, as shown in FIG. 22, in the special observation mode, the LED light source control unit 604 inserts the high pass filter 602 on the optical path of the B-LED 601c. In addition, the B-LED 601c is constantly lit, and ON/OFF of the R-LED 601a and the G-LED 601b is alternately repeated at fixed intervals. Accordingly, blue light in which light having a wavelength in a wavelength band of 450 nm or less is cut off and mixed color light of green light, red light, and blue light in which light having a wavelength in a wavelength band of 450 nm or less is cut off are alternately emitted to the observation target.

Then, in the imaging control unit 49, a signal charge obtained by imaging the observation target under the blue light in which light having a wavelength in a wavelength band of 450 nm or less is cut off is read in a reading period of the first frame, and the B1 image signal is output. Then, a signal charge obtained by imaging the observation target under the mixed color light is read in a reading period of the second frame, and the B2 image signal, the G2 image signal, and the R2 image signal are output. Subsequent processing can be performed in the same manner as in the endoscope system 10.

Figure 23:
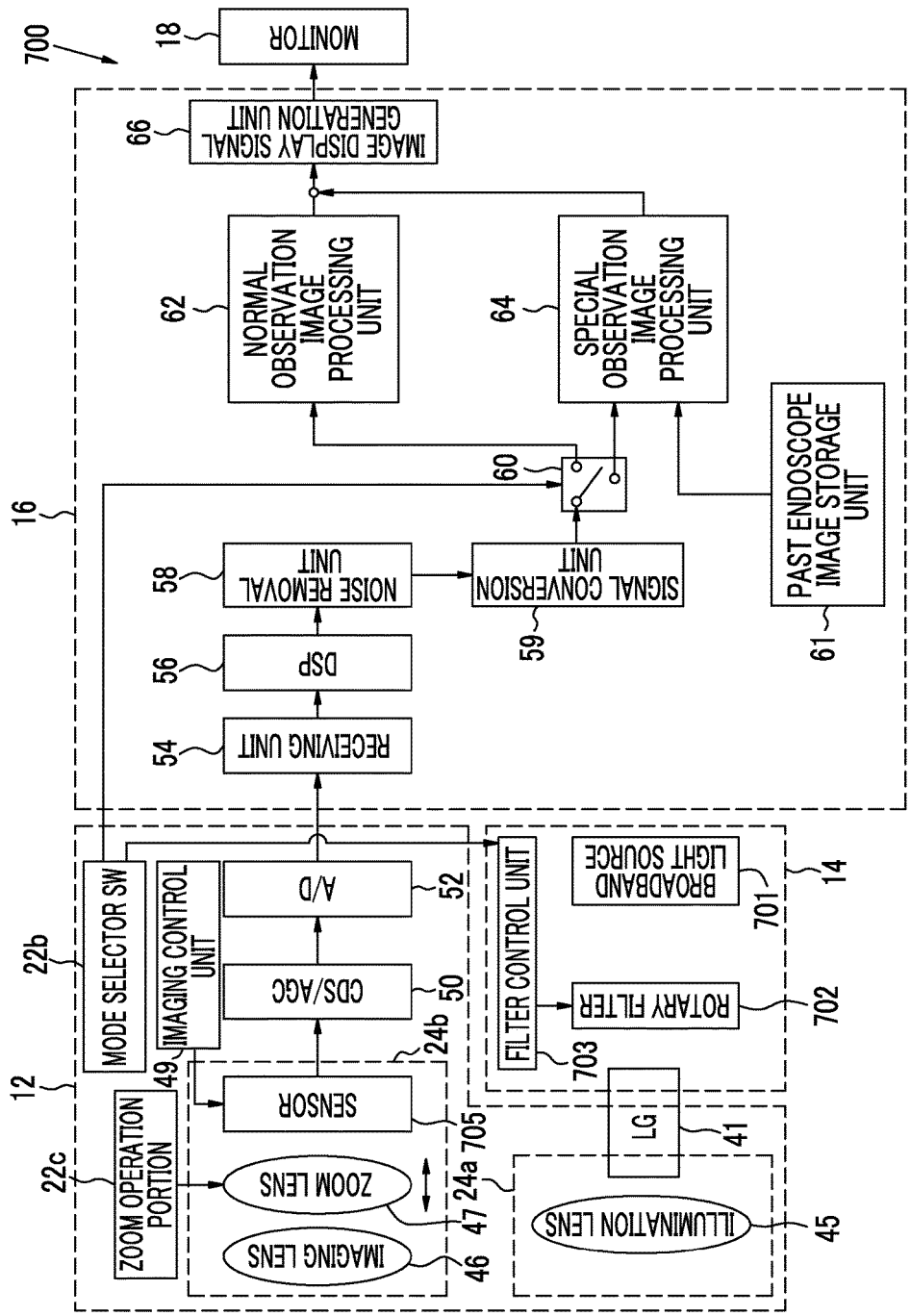
FIG. 23 is a block diagram of a rotary filter type endoscope system.

As shown in FIG. 23, in a light source device 14 of a rotary filter type endoscope system 700, a broadband light source 701, a rotary filter 702, and a filter control unit 703 are provided instead of the first and second blue laser light sources 34 and 36 and the light source control unit 40. A sensor 705 of the endoscope system 700 is a monochrome imaging device in which no color filter is provided. In addition, the DSP 56 does not perform processing specific to the color sensor, such as demosaic processing for generating a signal of missing color of each pixel. Other than these, the endoscope system 700 is the same as the endoscope system 10.

The broadband light source 701 is, for example, a xenon lamp or a white LED, and emits white light having a wavelength in a wavelength band ranging from blue to red. The rotary filter 702 includes a normal observation mode filter 710 and a special observation mode filter 711 (refer to FIG. 24), and can move in a radial direction between a first position for normal observation mode to place a normal observation mode filter 710 on the optical path, in which the white light emitted from the broadband light source 701 is incident on the light guide 41, and a second position for special observation mode to place a special observation mode filter 711 on the optical path. The movement of the rotary filter 702 between the first and second positions is controlled by the filter control unit 703 according to the selected observation mode. In addition, the rotary filter 702 rotates according to the imaging frame of the sensor 705 while being placed at the first or second position.

Figure 24:
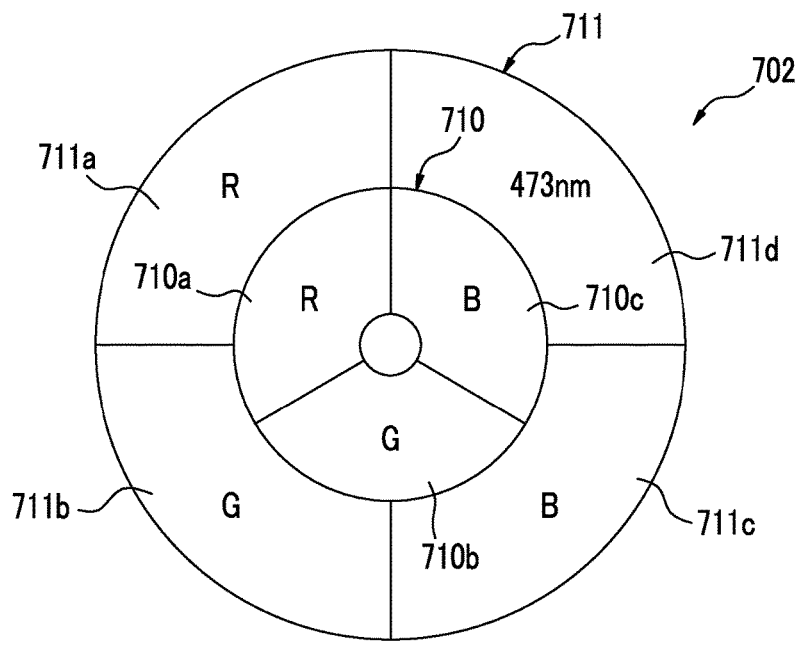
FIG. 24 is a plan view of a rotary filter.

As shown in FIG. 24, the normal observation mode filter 710 is provided in the inner peripheral portion of the rotary filter 702. The normal observation mode filter 710 includes an R filter 710a that transmits red light, a G filter 710b that transmits green light, and a B filter 710c that transmits blue light. Therefore, when the rotary filter 702 is placed at the first position for normal light observation mode, the white light from the broadband light source 701 is incident on one of the R filter 710a, the G filter 710b, and the B filter 710c according to the rotation of the rotary filter 702. As a result, red light, green light, and blue light are sequentially emitted to the observation target according to the transmitted filter, and the sensor 705 outputs sequentially an R image signal, a G image signal, and a B image signal by imaging the observation target with reflected light of the red light, the green light, and the blue light.

The special observation mode filter 711 is provided in the outer peripheral portion of the rotary filter 702. The special observation mode filter 711 includes an R filter 711a that transmits red light, a G filter 711b that transmits green light, a B filter 711c that transmits blue light, and a narrowband filter 711d that transmits narrowband light of 473±10 nm. Therefore, when the rotary filter 702 is placed at the second position for normal light observation mode, the white light from the broadband light source 701 is incident on one of the R filter 711a, the G filter 711b, the B filter 711c, and the narrowband filter 711d according to the rotation of the rotary filter 702. As a result, red light, green light, blue light, and narrowband light (473 nm) are sequentially emitted to the observation target according to the transmitted filter, and the sensor 705 outputs sequentially an Rx image signal, a Gx image signal, a Bx image signal, and a narrowband image signal by imaging the observation target with reflected light of the red light, the green light, the blue light, and the narrowband light.

The Rx image signal and the Gx image signal acquired in the special observation mode correspond to the R2 image signal and the G2 image signal in the first to fifth embodiments. In addition, the narrowband image signal acquired in the special observation mode corresponds to the B1 image signal in the first to fifth embodiments, and the Bx image signal corresponds to the B2 image signal in the first to fifth embodiments. Accordingly, subsequent processing can be performed in the same manner as in the endoscope system 10.

Although the CCD image sensor is used as the sensor 48 in the first to fifth embodiments, a complementary metal oxide semiconductor (CMOS) image sensor may also be used as the sensor 48. In this case, the CMOS image sensor is driven in a so-called rolling shutter method, and accumulation and reading of the signal charge are sequentially performed for each row (each of first to N-th rows) of pixels.

For this reason, the timing of the accumulation and reading of the signal charge of each row differs according to each row. Therefore, switching between the first white light and the second white light is preferably performed in accordance with the reading timing.

Figure 25:
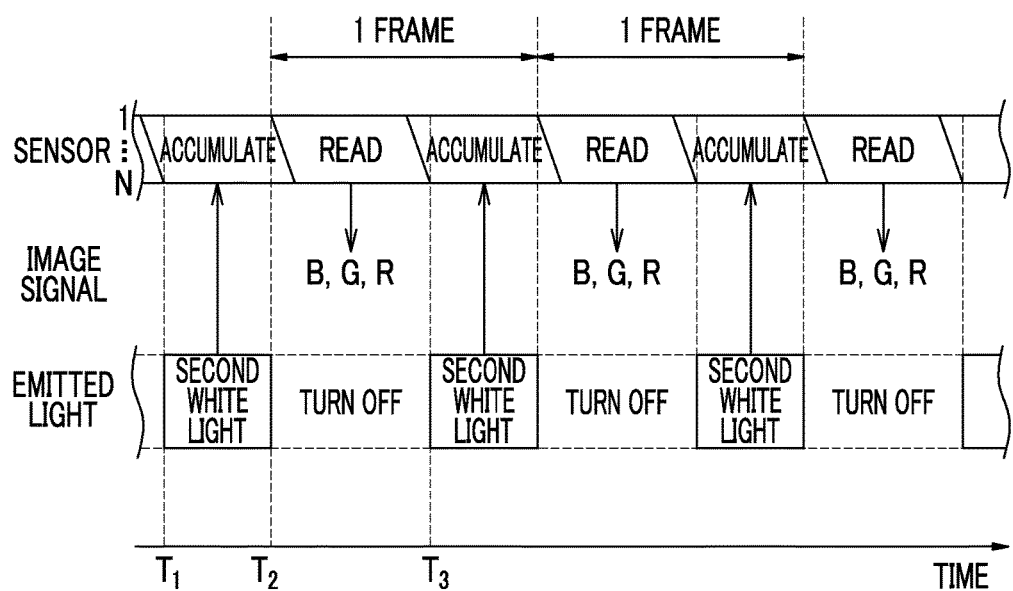
FIG. 25 is an explanatory diagram showing the imaging control in the normal observation mode when a sensor is a CMOS.
Figure 26:
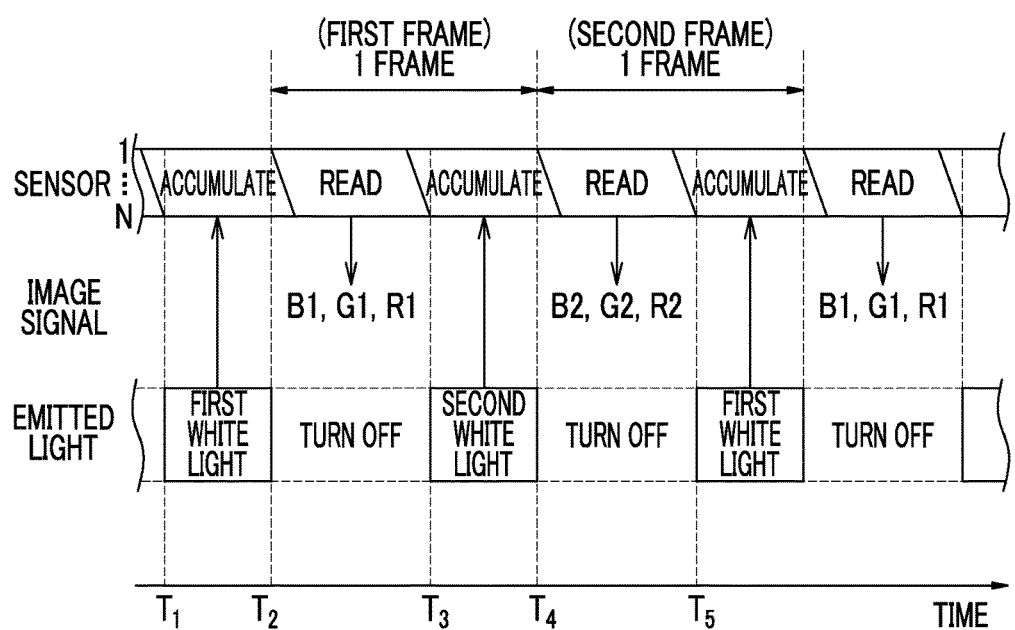
FIG. 26 is an explanatory diagram showing the imaging control in the special observation mode when a sensor is a CMOS.

For example as shown in FIG. 25, in the normal observation mode, the emission of the second white light is performed until the accumulation of the first row is completed (time T2) from the start of the accumulation of the N-th row (time T1), while the emission of the second white light is stopped until the reading of the N-th row is completed (time T3) from the start of the reading of the first row (time T2). In addition, as shown in FIG. 26, in the special observation mode, the emission of the second white light is performed until the accumulation of the first row is completed (time T2) from the start of the accumulation of the N-th row (time T1), while the emission of the second white light is stopped until the reading of the N-th row is completed (time T3) from the start of the reading of the first row (time T2). After switching from the second white light to the first white light, the emission of the first white light is performed until the accumulation of the first row is completed (time T4) from the start of the accumulation of the N-th row (time T3), while the emission of the first white light is stopped until the reading of the N-th row is completed (time T5) from the start of the reading of the first row (time T4).

Thus, it is possible to standardize the length (exposure) of the substantial charge accumulation period of each row and to prevent the first white light and the second white light from being mixed. Therefore, even if a CMOS image sensor is used as the sensor 48, it is possible to calculate an accurate oxygen saturation as in the embodiments described above. The same is true for a case when the LED light source unit 701 or the broadband light source 701 and the rotary filter 702 are used instead of the first and second blue laser light sources 34 and 36.

In addition, although the current oxygen saturation image is generated based on the current oxygen saturation corrected by the oxygen saturation correction section 80 and the past oxygen saturation image is generated based on the past oxygen saturation after correction in the first to fourth embodiments, it is also possible to calculate a difference between the current oxygen saturation and the past oxygen saturation and generate and display the difference image based on the difference.

Figure 27:
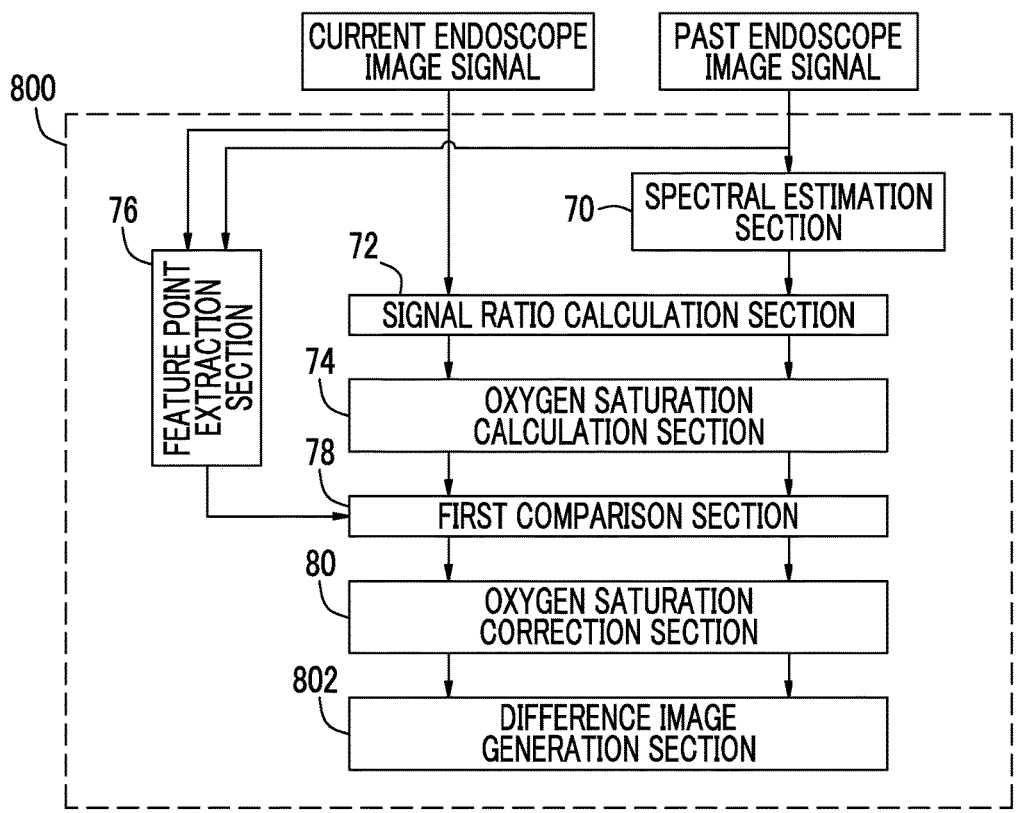
FIG. 27 is a block diagram of a special observation image processing unit including a difference image generation section.

In order to generate the difference image, as shown in FIG. 27, a difference image generation section 802 is provided in a special observation image processing unit 800. The special observation image processing unit 800 has the same configuration as the special observation image processing unit 64 except that the difference image generation section 802 is provided instead of the oxygen saturation image generation section. The difference image generation section 802 calculates a difference between the current oxygen saturation corrected by the oxygen saturation correction section 80 and the past oxygen saturation corrected similarly by the oxygen saturation correction section 80.

The difference image generation section 802 generates a difference image by imaging the calculated difference. The generated difference image is displayed on the monitor 18. Accordingly, the difference is highlighted on the monitor 18. As a method of generating the difference image, for example, a method can be considered in which a color table (not shown) obtained by matching a difference between the current oxygen saturation and the past oxygen saturation with a color corresponding to the difference is provided in the difference image generation section 802 and the color corresponding to the difference value is assigned with reference to the color table. In addition, the difference image generation section 802 may generate a difference image by calculating the difference without correcting the current or past oxygen saturation using the oxygen saturation correction section 80.

Although the difference image generation section 802 calculates the difference between the current oxygen saturation and the past oxygen saturation, it is also possible to compare a current oxygen saturation image with a past oxygen saturation image and generate and display a difference image based on the difference. As an example of the difference between the current oxygen saturation image and the past oxygen saturation image, a difference of color information, such as a signal value of the color difference signal, can be considered. In addition, although the first past oxygen saturation image is generated based on the first past oxygen saturation and the second past oxygen saturation image is generated based on the second past oxygen saturation numerical image in the fifth embodiment, it is also possible to calculate a difference between the first past oxygen saturation and the second past oxygen saturation and generate a difference image based on the difference. When the second past oxygen saturation image is used instead of the second oxygen saturation numerical image, the first oxygen saturation image and the second oxygen saturation image may be compared with each other, and the difference image may be generated and displayed based on the difference (difference value of color information, such as a color difference signal).

In the first to eighth embodiments, the oxygen saturation is calculated. However, instead of or in addition to the oxygen saturation, other biological function information, such as an oxygenated hemoglobin index that is calculated from "blood volume (signal ratio R2/G2)×oxygen saturation (%)" or a reduced hemoglobin index that is calculated from "blood volume×(1−oxygen saturation) (%)", may be calculated.

What is claimed is:

1. An endoscope system comprising:
a processor device that generates a spectral estimation image from a normal observation image obtained by imaging a subject using white light, calculates a first oxygen saturation from the spectral estimation image, and generates a first oxygen saturation image from the first oxygen saturation; and
an endoscope including a narrowband light source emitting a specific wavelength corresponding with oxygen saturation, endoscope imaging the subject by special observation mode using the narrowband light having the specific wavelength,
wherein the processor device generates a second oxygen saturation image for display based on the imaging of the subject by the endoscope and displays the first oxygen saturation image and the second oxygen saturation image.

2. The endoscope system according to claim 1, wherein the processor device further calculates a second oxygen saturation based on the imaging of the subject by the endoscope and compares the first oxygen saturation with the second oxygen saturation.

3. The endoscope system according to claim 2, wherein the processor device further corrects at least one of the first and second oxygen saturations based on a comparison result of the processor device.

4. The endoscope system according to claim 3,
wherein the processor device corrects at least one of the first and second oxygen saturations using gain processing and/or shift processing for oxygen saturation correction.

5. The endoscope system according to claim 4, wherein the processor device further determines whether or not to correct at least one of the first and second oxygen saturations based on a comparison result of the processor device.

6. The endoscope system according to claim 3, wherein the processor device further determines whether or not to correct at least one of the first and second oxygen saturations based on a comparison result of the processor device.

7. The endoscope system according to claim 3, wherein the processor device extracts feature points from the normal observation image and extracts feature points from a specific image used to calculate the second oxygen saturation,
wherein the processor device compares an oxygen saturation of a first feature point among the feature points of the normal observation image with an oxygen saturation of a second feature point among the feature points of the specific image, the second feature point having the same feature quantity as the first feature point.

8. The endoscope system according to claim 3, wherein the processor device extracts feature points from the normal observation image and extracts feature points from an oxygen saturation numerical image having numerical information of the second oxygen saturation for each pixel,
wherein the processor device compares an oxygen saturation of a first feature point among the feature points of the normal observation image with an oxygen saturation of a second feature point among the feature points of the oxygen saturation numerical image, the second feature point having the same feature quantity as the first feature point.

9. The endoscope system according to claim 3,
wherein the processor device compares a distribution of the first oxygen saturation with a distribution of the second oxygen saturation.

10. The endoscope system according to claim 2, wherein the processor device further corrects a matrix coefficient based on a comparison result of the processor device, the matrix coefficient being used to generate the spectral estimation image.

11. The endoscope system according to claim 2, wherein the processor device further:
performs display processing for displaying a specific range and a range outside the specific range in different display methods in the first oxygen saturation image and displaying a specific range and a range outside the specific range in different display methods in the second oxygen saturation image, the first oxygen saturation in the specific range of the first oxygen saturation image being set in advance and the second oxygen saturation in the specific range of the second oxygen saturation image being set in advance; and
corrects a boundary value of the specific range based on a comparison result of the processor device.

12. The endoscope system according to claim 11,
wherein the processor device performs the comparison based on a difference between the oxygen saturation of the first feature point and the oxygen saturation of the second feature point.

13. The endoscope system according to claim 2, wherein the processor device further extracts feature points from the normal observation image and extracts feature points from a specific image used to calculate the second oxygen saturation,
wherein the processor device compares an oxygen saturation of a first feature point among the feature points of the normal observation image with an oxygen saturation of a second feature point among the feature points of the specific image, the second feature point having the same feature quantity as the first feature point.

14. The endoscope system according to claim 2, wherein the processor device extracts feature points from the normal observation image and extracts feature points from an oxygen saturation numerical image having numerical information of the second oxygen saturation for each pixel,
wherein the processor device compares an oxygen saturation of a first feature point among the feature points of the normal observation image with an oxygen saturation of a second feature point among the feature points of the oxygen saturation numerical image, the second feature point having the same feature quantity as the first feature point.

15. The endoscope system according to claim 14,
wherein the processor device performs the comparison based on a difference between the oxygen saturation of the first feature point and the oxygen saturation of the second feature point.

16. The endoscope system according to claim 2,
wherein the processor device compares a distribution of the first oxygen saturation with a distribution of the second oxygen saturation.

17. The endoscope system according to claim 2, wherein the processor device generates a difference image by imaging a difference between the first and second oxygen saturations or a difference between the first and second oxygen saturation images,
wherein the difference image is displayed.

18. An operation method for the endoscope system according to claim 1, comprising:
a step of generating a spectral estimation image by performing spectral estimation processing on a normal observation image with the processor device;
a step of calculating a first oxygen saturation based on the spectral estimation image with the processor device;
a step of generating a first oxygen saturation image from the first oxygen saturation with the processor device; and
a step of displaying the first oxygen saturation image and a second oxygen saturation image based on a second oxygen saturation with a display.

19. The endoscope system according to claim 1,
wherein the first oxygen saturation image and the second oxygen saturation image are displayed at the same time.

* * * * *